(12) United States Patent
Dines et al.

(10) Patent No.: US 6,876,879 B2
(45) Date of Patent: *Apr. 5, 2005

(54) MAMMOGRAPHY METHOD AND APPARATUS

(75) Inventors: Kris A. Dines, Indianapolis, IN (US); Elizabeth Kelly-Fry, Indianapolis, IN (US); Ada Patricia Romilly, Indianapolis, IN (US)

(73) Assignee: XDATA Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/394,945

(22) Filed: Mar. 21, 2003

(65) Prior Publication Data

US 2003/0167004 A1 Sep. 4, 2003

Related U.S. Application Data

(63) Continuation of application No. 09/448,675, filed on Nov. 24, 1999, now Pat. No. 6,754,499.
(60) Provisional application No. 60/109,991, filed on Nov. 25, 1998.

(51) Int. Cl.[7] .............................. A61B 6/00; A61B 8/00; A61B 10/00
(52) U.S. Cl. ....................... 600/427; 600/439; 128/915; 128/916; 378/37
(58) Field of Search .................................. 600/439, 407, 600/427, 437; 128/915, 916; 378/37

(56) References Cited

U.S. PATENT DOCUMENTS

| 5,474,072 A | 12/1995 | Shmulewitz |
| 5,479,927 A | 1/1996 | Shmulewitz |
| 5,562,095 A | 10/1996 | Downey et al. |
| 5,582,173 A | 12/1996 | Li |
| 5,603,326 A | 2/1997 | Richter |

(Continued)

FOREIGN PATENT DOCUMENTS

| WO | WO 9511627 | 5/1995 | |
| WO | 96-06334 | * 2/1998 | ........... A61B/10/00 |

OTHER PUBLICATIONS

Solid Breast Nodules: Use of Sonography to Distinguish Between Benign and Malignant Lesions, Radiology 196, pp. 123–134, 1995.

(Continued)

*Primary Examiner*—Shawna J. Shaw
(74) *Attorney, Agent, or Firm*—Doreen J. Gridley; Rachel L. St. Peter; Ice Miller

(57) ABSTRACT

A system for generating a three-dimensional image of the compressed breast 40 of a subject includes an x-ray mammography unit 24 for generating x-ray mammography data, a mechanical scanner 20 including an x-ray mammography compression paddle assembly 22, a control and motion system 26, 28 for driving the mechanical scanner 20 and for sensing the control and motion system's position, an ultrasound probe 32 for generating ultrasound image data in spatial registration with the x-ray mammography unit 24, and a computer 38 for generating from the ultrasound image data and the x-ray mammography data the three-dimensional ultrasound image. A method of examining a breast of a subject includes contacting an anterior surface of the breast with a compression paddle, applying pressure to the anterior surface of the breast with the compression paddle to compress it to reduce the thickness of the breast tissue, passing an ultrasound beam having a frequency greater than 3 MHz, preferably about 5 MHZ or more, through the paddle and the compressed breast tissue, receiving echoes from the compressed breast tissue through the compression paddle, and converting the echoes into breast examination data.

21 Claims, 17 Drawing Sheets

U.S. PATENT DOCUMENTS

| | | | |
|---|---|---|---|
| 5,640,956 | A | 6/1997 | Getzinger et al. |
| 5,660,185 | A | 8/1997 | Shmulewitz et al. |
| 5,662,109 | A | 9/1997 | Hutson |
| 5,664,573 | A | 9/1997 | Shmulewitz |
| 5,776,062 | A | 7/1998 | Nields |
| 5,787,889 | A | 8/1998 | Edwards et al. |
| 5,840,022 | A | 11/1998 | Richter |
| 5,842,473 | A | 12/1998 | Fenster et al. |
| 5,851,180 | A | 12/1998 | Crosby et al. |
| 5,934,288 | A | 8/1999 | Avila et al. |
| 5,938,613 | A | 8/1999 | Shmulewitz |
| 6,102,866 | A | 8/2000 | Nields et al. |
| 6,254,538 | B1 * | 7/2001 | Downey et al. ............ 600/439 |
| 6,574,499 | B1 * | 6/2003 | Dines et al. ................ 600/427 |
| 2003/0149364 | A1 * | 8/2003 | Kapur et al. ................ 600/439 |

OTHER PUBLICATIONS

Factors Critical to Highly Accurate Diagnosis of Malignant Breast Pathologies by Ultrasound Imaging, Ultrasound 82, eds., Lerski, R. A., et al, Pergamon Press, Oxford and New York, 1983.

Breast Ultrasound: Report of a 5–Year Combined Clinical and Research Program, Le Journal Francais d'Echographie, 2n 5, pp. 133–139, 1984.

Classification and Diagnostic Criteria in Breast Echography, Japan Journal of Medical Ultrasonics, vol. 13, No. 1, pp. 19–31, 1986 (in English).

Dynamic Test in Real–Time Breast Echography, Ultrasound in Med. & Biology, 14 (supp. 1), pp. 53–57, 1998.

Clinical Evaluation of Ultrasound in Breast Cancers in Comparison with Mammography, Computed Tomography and Digital Subtraction Angiography, Topics in Breast Ultrasound, eds., Kasumi, F., et al., Shinohara Pub. Inc., Tokyo, Japan 1991.

Comparison of X–ray Mammograpy and Sonomammography of 1,209 Histologically Verified Breast Diseases, Breast Ultrasound Update, eds., Madjar, H., et al, Karger, Basel, Freiburg, New York 1994, pp. 40–50.

Clinical Program of Breast Surveillance by Means of Echopalpation: Results from Jan. 1985 to May 1992, Breast Ultrasound Update, eds., Madjar, H., et al, Karger, Basel, Freiburg, New York, 1994, pp. 51–62.

Is Breast Sonography an Additional Method for the Diagnosis of Palpable Masses, Topics in Breast Ultrasound, eds., Kasumi, F., et al, Shinohara Pub. Inc., 11–7 Hongo 2–chome, Bunkyo–ku, Tokyo 113, Japan, 1991.

Imaging Techniques Other Than Mammography For the Detection and Diagnosis of Breast Cancer, Recent Results in Cancer Research, 119, p. 127–135, 1990.

The Role of US in Breast Imaging, Radiology, 117, pp. 305–311, 1990.

Breast Sonography, American Journal of Radiology, 156 (3), pp. 449–455, 1991.

Breast Masses: Mammographic and Sonographic Evaluation, Radiol. Clin. North Am., 30, pp. 67–92, 1992.

Nonmammographic Imaging of the Breast: Current issues and Future Prospects , Sem. In Roentgenology, XXVIII. No. 3, pp. 231–241, 1993.

Indications for and Comparative Diagnostic Value of Combined Ultrasound and X–ray Mammography, European Journal of Radiology, 3, 1983, pp. 229–302.

A New Ultrasound Mammography Technique That Provides Improved Correlation with X–ray Mammography, Amer. Col. Radiol., 24th National Conference on Breast Cancer, New Orleans, LA, Mar. 1990.

Adaption, Development and Expansion of X–ray Mammography Techniques for Ultrasound Mammography, Journal of Ultrasound in Medicine, 10, No. 3, supplement, Mar. 1991.

New Techniques for Ultrasound Mammography, National Cancer Institute Breast Imaging Workshop, Bethesda, MD, Sep. 4–6, 1991, pp. 1–15.

Rapid Ultrasound Scanning of Both Breasts Positioned and Compressed in the Mode of X–ray Mammography, Journal of Ultrasound in Medicine, 13, No. 3, supplement, Mar., 1994.

Automated Three–Dimensional Ultrasound Breast Scanning in the Crainocaudal Mammography Position, Ninth International Congress on the Ultrasonic Examination of the Breast, Sep. 28–Oct. 1, 1995, pp. 43–44.

Clinical Evaluation of Manual, Automated, and 3–D Ultrasound Imaging of Breasts Compressed Mammography Instrumentation for Combined X–ray and Ultrasound Imaging, Ninth International Congress on the Ultrasonic Examination of the Breast, Sep. 28–Oct. 1, 1995, pp. 45–46.

Mammgraphy Instrumentation for Combined X–ray and Ultrasound Imaging, Ninth International Congress on the Ultrasonic Examination of the Breast, Sep. 28–Oct. 1, 1995, pp. 40–42.

Technique for Detecting and Evaluating Breast Lesions, Journal of Ultrasound in Medicine, 13, pp. 797–802, 1994.

Detection of Diffuse Breast Cancers with a New Sonographic Method, J. Clin. Ultrasound, 24, pp. 157–168, May, 1996.

Description and First Clinical Use of a New System for Combined Mammography and Automated Clinical Amplitude/Velocity Reconstructive Imaging (CARI) Breast Sonography, Invest. Radiol., 32, pp. 19–28, 1997.

Detection of Malignant and Benign Breast Lesions with an Automated US System: Results in 120 Cases, Radiology, 205, pp. 823–830, 1997.

A Computer–Aided Three–Dimensional Display System for Ultrasonic Diagnosis of a Breast Tumor, Ultrasonic, pp. 261–268, Nov., 1979.

Three–Dimensional Imaging in Ultrasound, J. of Med. Systems, vol. 6, No. 6, pp. 579–589, 1982.

Three Dimensional Imaging of Solid Breast Tumors with Ultrasound: Preliminary Data and Analysis of Its Possible Contribution to the Understanding of the Standard Two–Dimensional Sonographic Images. Ultrasound Obstel. Gynecol., vol. 1, pp. 384–390, 1991.

Analysis of Normal Breast Tissue and of Solid Breast Masses Using Three–Dimensional Ultrasound Mammography, Ultrasound Obstet. Gynecol., vol. 14, pp. 114–124, 1999.

Stereoscopic Visualization of Three–Dimensional Ultrasonic Data Applied to Breast Tumors, Eur. J. Ultrasound, vol. 8, No. 1, pp. 51–65, Sep., 1998.

The Rationale for Ultrasound Imaging of Breasts Compressed and Positioned in the Modes Applied in X–ray Mammography, International Breast Ultrasound School, Sep. 28–Oct. 1, 1995, pp. 126–129.

Product News Section, Journal of Ultrasound in Medicine, vol. 19, No. 2, Feb. 2000.

* cited by examiner

MAMMOGRAPHY METHOD AND APPARATUS

RELATED APPLICATIONS

This is a continuation application of U.S. patent application Ser. No. 09/448,675, filed Nov. 24, 1999, now U.S. Pat. No. 6,574,499, which is based on U.S. provisional application Ser. No. 60/109,991, filed Nov. 25, 1998, the disclosures of which are hereby incorporated herein by reference.

The U.S. Government has a paid-up license in this invention and the right in limited circumstances to require the patent owner to license others on reasonable tams as provided for by the terms of NIH Grant Number 2 R44 CA65225 awarded by the National Institutes of Health.

FIELD OF THE INVENTION

This invention relates to mammography methods and to apparatus for carrying out such methods.

BACKGROUND OF THE INVENTION

Currently, on an international scale, ultrasound breast examination is an accepted medical modality applied both as a primary method for evaluation of the breasts of young patients, that is, those under 40 years of age, and as an adjunct to x-ray mammography. See, for example, Kasumi, F., et al., "Topics in Breast Ultrasound," Seventh International Congress on the Ultrasonic Examination of the Breast, Shinohara Publications, Inc., 1–7, Hongo 2-chome, Bunkyo-ku, Tokyo 113, Japan, 1991; Tohno, E., et al., *Ultrasound Diagnosis of Breast Diseases*, New York, Churchill-Livingstone, 1994; and, Stavros, A. T., et al., "Solid Breast Nodules: Use of Sonography to Distinguish Between Benign and Malignant Lesions," Radiology 196, pp. 123–134, 1995. In terms of the diagnostic effectiveness of the ultrasound breast imaging, a number of investigators from the early 1980s to the present have shown that this modality is not limited to diagnosing the solid or cystic nature of a breast mass. It is capable, with a high degree of accuracy, of providing imaging data which permits differentiation of benign and malignant breast masses. See, for example, Stavros, A. T., et al., "Solid Breast Nodules: Use of Sonography to Distinguish Between Benign and Malignant Lesions," Radiology 196, pp. 123–134, 1995; Kelly-Fry, E., et al., "Factors Critical to Highly Accurate Diagnosis of Malignant Breast Pathologies by Ultrasound Imaging," Ultrasound 82, eds., Lerski, R. A., et al., Pergamon Press, Oxford and New York, 1983; Harper, P., et al., "Breast Ultrasound: Report of a 5-Year Combined Clinical and Research Program," Le Journal Francais d'Echographie, 2n 5, pp. 133–139, 1984; Ueno, E., et al., "Classification and Diagnostic Criteria in Breast Echography," Japan Journal of Medicine, Ultrasonics, vol. 13, no. 1, pp. 19–31, 1986 (in English); Ueno, E., et al., "Dynamic Tests in Real-Time Breast Echography," Ultrasound in Med. & Biology, 14 (supp. 1), pp. 53–57, 1988; Tohnosu, N., et al., "Clinical Evaluation of Ultrasound in Breast Cancers in Comparison with Mammography, Computed Tomography and Digital Subtraction Angiography," Topics in Breast Ultrasound, eds., Kasumi, F., et al., Shinohara Pub. Inc., Tokyo, Japan, 1991; and, Gerlach, B., et al., "Comparison of X-ray Mammography and Sonomammography of 1,209 Histological Verified Breast Diseases," Breast Ultrasound Update, eds., Madjar, H., et al., Karger, Basel, Freiburg, N.Y., 1994. In Japan, ultrasound breast imaging has equal diagnostic status with x-ray mammography. See, for example, Ueno, E., et al., "Classification and Diagnostic Criteria in Breast Echography," Japan Journal of Medicine, Ultrasonics, vol. 13, no. 1, pp. 19–31, 1986 (in English); Ueno, E., et al., "Dynamic Tests in Real-Time Breast Echography," Ultrasound in Med. & Biology, 14 (supp. 1), pp. 53–57, 1988; Tohnosu, N., et al., "Clinical Evaluation of Ultrasound in Breast Cancers in Comparison with Mammography, Computed Tomography and Digital Subtraction Angiography," Topics in Breast Ultrasound, eds., Kasumi, F., et al., Shinohara Pub. Inc., Tokyo, Japan, 1991. European investigators have found that ultrasound breast imaging can equal the accuracy of x-ray mammography in the diagnosis of overt, malignant breast masses. See, for example, Gerlach, B., et al., "Comparison of X-ray Mammography and Sonomammography of 1,209 Histologically Verified Breast Diseases," Breast Ultrasound Update, eds., Madjar, H., et al., Karger, Basel, Freiburg, N.Y., 1994; Dambrosio, F., et al., "Clinical Program of Breast Surveillance by Means of Echopalpation: Results from January 1985 to May 1992," Breast Ultrasound Update, eds., Madjar, H., et al., Karger, Basel, Freiburg, N.Y., 1994; and, Leucht, W., et al., "Is Breast Sonography an Additional Method for the Diagnosis of Palpable Masses," Topics in Breast Ultrasound, eds., Kasumi, F., et al., Shinohara Pub. Inc., 11–7 Hongo 2-chome, Bunkyo-ku, Tokyo 113, Japan, 1991. In the United States, many clinicians during the 1980s and early 1990s restricted ultrasound breast imaging to a limited role of differentiation between cystic and solid masses. See, for example, Sickles, E. A., "Imaging Techniques Other Than Mammography for the Detection and Diagnosis of Breast Cancer," Recent Results in Cancer Research, 119, pp. 127–135, 1990; Jackson, V. P., "The Role of US in Breast Imaging," Radiology, 177, pp. 305–311, 1990; Bassett, L. W., et al., "Breast Sonography," American Journal of Radiology, 156 (3), pp. 449–455, 1991; Feig, S. A., "Breast Masses: Mammographic and Sonographic Evaluation," Radiol. Clin. North Am., 30, pp. 67–93, 1992; and, Orel, S. G., et al., "Nonmammographic Imaging of the Breast: Current Issues and Future Prospects," Sem. In Roentgenology, XXVIII, no. 3, pp. 231–241, 1993. Following the 1995 publication of a clinical study which provided further data on the successful differentiation of benign and malignant masses by ultrasound breast imaging techniques, this modality was more widely applied in the United States. See, for example, Stavros, A. T., et al., "Solid Breast Nodules: Use of Sonography to Distinguish Between Benign and Malignant Lesions," Radiology 196, pp. 123–134, 1995.

Since the 1980s, most ultrasound breast examinations have been carried out with the patient in the supine position. Imaging is carried out by moving a handheld ultrasound transducer across the free flowing surface of the breast and recording the images on film. By contrast, for x-ray mammography, the patient is in a standing or sitting position with the breast compressed between a plastic paddle and the surface of an x-ray film holder module. The breast is alternately compressed in various orientations such as cranio-caudal, lateral and oblique while the x-ray beam traverses the breast in each of these positions. For each individual position, an image is recorded. Currently, to correlate precisely standard breast ultrasound imaging data with that provided by x-ray mammography data can sometimes be impossible because the anatomical orientations of tissues traversed by the x-ray beam for the various compressed breast positions are different from the anatomical position of tissues traversed by the ultrasound beam following its entrance into an uncompressed breast in a supine position. Also, since tissue is mobile, the location of a breast mass as imaged when a breast is compressed between two plates can be different from that of its imaged location when the breast is uncompressed and in a supine position. These problems can lead to diagnostic errors.

In an attempt to improve correlation between ultrasound and x-ray imaging data, in 1983 Novak demonstrated a technique for holding the breast in the same positions used in x-ray mammography while applying a linear array ultrasound transducer in direct contact with the breast surface. See, Novak, D., "Indications for and Comparative Diagnostic Value of Combined Ultrasound and X-ray Mammography," European Journal of Radiology, 3, 1983. A plexiglas plate was used as a support on one side of the breast while the ultrasound transducer contacted the skin surface of the opposite side. The breast was not compressed between two plates.

In the early 1990s, Kelly-Fry, et al., demonstrated that specially designed breast compression paddles, constructed from various types and thicknesses of plastics, including polyesters, polycarbonates and acrylics, can transfer both x-ray and ultrasound, without serious attenuation of either modality. See, for example: Kelly-Fry, E., et al., "A New Ultrasound Mammography Technique That Provides Improved Correlation With X-ray Mammography," Amer. Col. Radiol., 24th National Conference on Breast Cancer, New Orleans, La., March 1990; Kelly-Fry, E., et al., "Adaptation, Development and Expansion of X-ray Mammography Techniques for Ultrasound Mammography," Journal of Ultrasound in Medicine, 10, no. 3, S 16, supplement, March 1991; Kelly-Fry, E., "New Techniques for Ultrasound Mammography," National Cancer Institute Breast Imaging Workshop, Bethesda, Md., Sep. 4–6, 1991; and, Kelly-Fry, E., et al., "Rapid Ultrasound Scanning of Both Breasts Positioned and Compressed in the Mode of X-ray Mammography," Journal of Ultrasound in Medicine, 13, no. 3, S41–42 supplement, March, 1994. Instrumentation systems which incorporated these compression paddles were designed and applied to patients with the purpose of ultrasonically imaging a breast while it was held under the same compression and position orientations used in x-ray mammography. A hand-held ultrasound linear array transducer placed in contact with the compression plate was used for imaging.

Subsequent investigations of this approach by Dines, et al., Romilly-Harper, et al., and Kelly-Fry, et al., included automation of the transducer motion, use of high ultrasound frequencies, such as, for example, 7.5 MHz, 10 MHz and 13 MHz, 3D ultrasound imaging and clinical application of the system. See, for example, Dines, K. A., et al., "Automated Three-Dimensional Ultrasound Breast Scanning in the Craniocaudal Mammography Position," Ninth International Congress on the Ultrasonic Examination of the Breast, Sep. 28–Oct. 1, 1995, pp. 43–44; Dines, K. A., et al., "Automated Three-Dimensional Ultrasonic Breast Scanning in the Compressed Mammography Position," Journal of Ultrasound in Medicine, vol. 18, no. 3, supplement, March, 1999; Romilly-Harper, A. P., et al., "Clinical Evaluation of Manual, Automated and 3-D Ultrasound Imaging of Breasts Compressed in the Same Position Modes Applied in X-ray Mammography," Ninth International Congress on the Ultrasonic Examination of the Breast, Sep. 28–Oct. 1, 1995, pp. 45–46; and, Kelly-Fry, E., et al., "Mammography Instrumentation for Combined X-ray and Ultrasound Imaging," Ninth International Congress on the Ultrasonic Examination of the Breast, Sep. 28–Oct. 1, 1995.

To obtain data on the ultrasound attenuation and velocity of breast tumors, Richter designed a system in which a breast is compressed between two thick, for example, approximately 0.39 inch (10 mm), plexiglas plates, in the craniocaudal position. A metal reflector is placed on the inferior plexiglas plate and a linear array transducer is in contact with the upper plate. See, for example, Richter, K., "Technique for Detecting and Evaluating Breast Lesions," Journal of Ultrasound in Medicine, 13, pp. 797–802, 1994 and Richter, K. "Detection of Diffuse Breast Cancers with a New Sonographic Method," J. Clin. Ultrasound, 24, pp. 157–168, May, 1996. No x-ray imaging system was included in this initial instrumentation. The thick plexiglas compression paddle was inappropriate for x-ray breast imaging because of its increased attenuation of the x-ray beam. See, for example, Kelly-Fry, E., et al., "Mammography Instrumentation for Combined X-ray and Ultrasound Imaging," Ninth International Congress on the Ultrasonic Examination of the Breast, Sep. 28–Oct. 1, 1995. The thickness of the compression plate was also inappropriate for ultrasound imaging, causing increased ultrasound attenuation and multiple artifactual reflections within the breast image. In subsequent investigations, Richter, et al., carried out clinical studies at a low frequency, 5 MHz, using automated transducer motion with attachment of the imaging system to a standard x-ray unit. See, for example, Richter, et al., "Description and First Clinical Use of a New System for Combined Mammography and Automated Clinical Amplitude/Velocity Reconstructive Imaging (CARI) Breast Sonography, Invest. Radiol., 32, pp. 19–28, 1997, Richter, K., et al., "Detection of Malignant and Benign Breast Lesions with an Automated US System: Results in 120 Cases," Radiology, 205, pp. 823–830, 1997; 5,603,326; and, 5,840,022.

Other patents illustrate and describe instrument systems which combine x-ray mammography and ultrasound mammography using breast compression materials that are radiolucent and sonolucent. See, for example, U.S. Pat. Nos. 5,474,072; 5,479,927; and WO 95/11627. Earlier publications on the development and application of a combined x-ray and ultrasound mammography system using breast compression paddles that transmit both x-rays and ultrasound are not referenced. A breast examination system based upon these references was commercially marketed as a 3D ultrasound-guided breast biopsy system.

U.S. Pat. No. 5,776,062 illustrates and describes a system for applying x-rays to identify a region in a breast containing a possible malignant mass. Subsequently, ultrasound imaging is performed in order to target the x-ray identified region. Ultrasound-guided biopsy is then based on the combined data. The system is not designed for ultrasound scanning of the whole breast. Ultrasound imaging takes place via an opening in a substitute breast compression paddle, rather than via application of an ultrasound transducer in direct contact with the breast compression paddle used for the x-ray imaging. Interruption between the x-ray and ultrasound imaging procedures is required for this procedure.

With respect to 3-D ultrasound imaging, Itoh, et al., developed an early ultrasound instrumentation system which provided just the outlines, that is, the shape, in three dimensions, of a breast mass. See, for example, Itoh, et al., "A Computer-Aided Three-Dimensional Display System for Ultrasonic Diagnosis of a Breast Tumor," Ultrasonics, pp. 261–268, November, 1979. The 3-D images only included breast tumor contour outlines obtained by digitizing and computer processing image data from standard B-mode volume scans.

In 1982, J. F. Greenleaf carried out investigations of 3-D ultrasound imaging of excised breasts by digitizing and computer processing standard B-mode image data. See Greenleaf, J. F., "Three-Dimensional Imaging in Ultrasound," J. of Med. Systems, vol. 6, no. 6, pp. 580–589, 1982.

Rotten, et al., performed 3-D breast imaging using direct contact of a standard ultrasound transducer on the uncompressed breasts of subjects lying in supine position. See, for example, Rotten, D., et al., "Three Dimensional Imaging of Solid Breast Tumors With Ultrasound: Preliminary Data and Analysis of Its Possible Contribution to the Understanding of the Standard Two-Dimensional Sonographic Images," Ultrasound Obstet. Gynecol., vol. 1, pp. 384–390, 1991, and Rotten, D., et al., "Analysis of Normal Breast Tissue and of Solid Breast Masses Using Three-Dimensional Ultrasound Mammography," Ultrasound Obstet. Gynecol., vol. 14, 114–124, 1999. This image data was processed by a graphic work station with three-dimensional software. The system was not designed for a precise comparison between ultrasound images and x-ray images in terms of ultrasonically imaging a breast while it is held in the same positions and under the same compression for each modality.

Hernandez, et al., in an investigation of stereoscopic visualization of 3D ultrasound breast images used a plexiglas plate to compress a breast in a craniocaudal position. A linear phased array transducer was automatically translated across the compressed breast. The ultrasound imaging was not performed by directing the ultrasound through the plexiglas, but rather, by directing the ultrasound through an opening in the plexiglas. See Hernandez, A., et al., "Stereoscopic Visualization of Three-Dimensional Ultrasonic Data Applied to Breast Tumors," Eur. J. Ultrasound, vol. 8, no. 1, pp. 51–65, September 1998.

Various other apparatus and methods for conducting mammography are known. There are, for example, the methods and apparatus described in the following listed references: 5,640,956; 5,664,573; 5,938,613; Kelly-Fry, E., et al., "The Rationale For Ultrasound Imaging of Breasts Compressed and Positioned in the Modes Applied in X-ray Mammography," International Breast Ultrasound School, Sep. 28–Oct. 1, 1995, pp. 126–129. This background is not intended as a representation that a thorough search of the prior art has been conducted or that no more pertinent art than that listed above exists, and no such representation should be inferred.

Though x-ray mammography is a well-accepted imaging modality for breast cancer detection, it has several shortcomings. First of all, only a through-transmission image related to integrated tissue density is obtained. Overlying diagnostic features are summed together, resulting in the possibility that important information is blurred, summed, and overlaid so it cannot be detected in the x-ray image. A further shortcoming is that the breast is imaged only up to the chest wall, but there may be abnormalities further in that are not recorded on the x-ray film. The present invention provides an additional imaging view particularly appropriate for this latter situation.

DISCLOSURE OF THE INVENTION

According to one aspect of the invention, a system for generating a three-dimensional image of the compressed breast of a subject includes an x-ray mammography unit for generating x-ray mammography data, a mechanical scanner including an x-ray mammography compression paddle assembly, a control and motion system for driving the mechanical scanner and for sensing the control and motion system's position, an ultrasound probe for generating ultrasound image data in spatial registration with the x-ray mammography unit, and a computer for generating from the ultrasound image data and the x-ray mammography data the three-dimensional ultrasound image.

Illustratively according to this aspect of the invention, the ultrasound probe is a linear array probe.

Further illustratively according to this aspect of the invention, the apparatus includes a display for displaying the three-dimensional images.

Additionally illustratively according to this aspect of the invention, the apparatus includes a display for displaying two-dimensional ultrasound images.

Illustratively according to this aspect of the invention, the two-dimensional ultrasound images include B-mode images and the display for displaying two-dimensional ultrasound images is a display for displaying B-mode images.

Additionally illustratively according to this aspect of the invention, the apparatus includes an image capture device for capturing the B-mode images.

Illustratively according to this aspect of the invention, the x-ray mammography unit includes a vertical x-ray support column with a movable arm. The arm supports an x-ray tube. The x-ray mammography unit further includes a movable paddle mount block, a detector assembly including an x-ray image detector, and a lower compression surface for supporting the underside of the compressed breast.

Further illustratively according to this aspect of the invention, the mechanical scanner is connected to the compression paddle assembly. The compression paddle assembly is connected to the paddle mount block. Force applied by the paddle mount block compresses the breast under the compression paddle assembly.

Additionally illustratively according to this aspect of the invention, the movable arm can be rotated in a plane parallel to the patient's chest wall and positioned vertically so that the patient's breast can be inserted between the compression paddle assembly and the lower compression plate over a range of angular rotations of the movable arm.

Illustratively according to this aspect of the invention, the paddle mount block is mounted so as to permit it to be translated far enough to provide enough room for the patient's breast to fit between the compression paddle assembly and the detector assembly, for both the craniocaudal and lateral-oblique positions. Further, such translation is designed to permit the patient's body to fit between the compression paddle assembly and the detector assembly for imaging in the head-on position.

Further illustratively according to this aspect of the invention, the motion system includes a three-dimensional mechanical positioning system for scanning an ultrasound probe across the breast under control of the computer to yield a three-dimensional image registered to a spatial coordinate frame.

Additionally illustratively according to this aspect of the invention, the mechanical scanner includes at least one X-axis actuator, at least one Y-axis actuator, and a Z-axis positioner. Illustratively, at least one Y-axis actuator includes a left Y-axis actuator and a right Y-axis actuator. Further illustratively, the left Y-axis actuator and the right Y-axis actuator are attached in parallel to a support bar.

Illustratively according to this aspect of the invention, the X-axis actuator is mounted across the Y-axis actuators for positioning the Z-axis positioner carrying the ultrasound probe.

Further illustratively according to this aspect of the invention, the compression paddle assembly is fitted between the Y-axis actuators.

Additionally illustratively according to this aspect of the invention, the compression paddle assembly includes an ultrasound imaging compression paddle constructed from plastic. Illustratively, the plastic is a polycarbonate plastic.

Further illustratively according to this aspect of the invention, the apparatus includes a Z-axis position encoder for providing an input to the computer for use in three-dimensional image construction.

Illustratively according to this aspect of the invention, the Z-axis position encoder includes an encoder linkage, a linear encoder sensor, and a linear encoder graticule for monitoring the Z-position of the ultrasound probe.

According to another aspect of the invention, a method of examining a breast of a subject includes contacting an anterior surface of the breast with a compression paddle, applying pressure to the anterior surface of the breast with the compression paddle to compress it to reduce the thickness of the breast tissue between the compression paddle and the anterior wall of the subject's chest, passing an ultrasound beam having a frequency of greater than 3 MHz, preferably about 5 MHz or more, through the paddle and the compressed breast tissue, receiving echoes from the compressed breast tissue through the compression paddle, and converting the echoes into breast examination data.

Illustratively according to this aspect of the invention, contacting an anterior surface of the breast of the subject includes contacting an anterior surface of the breast of a standing subject.

Alternatively illustratively according to this aspect of the invention, contacting an anterior surface of the breast of the subject includes contacting an anterior surface of the breast of a sitting subject.

Further illustratively according to this aspect of the invention, contacting an anterior surface of the breast with a compression paddle includes contacting an anterior surface of the breast with a compression paddle constructed from plastic.

Additionally illustratively according to this aspect of the invention, contacting an anterior surface of the breast with a compression paddle constructed from plastic includes contacting an anterior surface of the breast with a compression paddle constructed from a polycarbonate plastic.

Illustratively according to this aspect of the invention, contacting an anterior surface of the breast with a compression paddle includes contacting an anterior surface of the breast with a compression paddle having a thickness not greater than about 0.12 inch (about 3 mm).

Further illustratively according to this aspect of the invention, applying pressure to the anterior surface of the breast with the compression paddle to compress it includes applying pressure to the anterior surface of the breast with the compression paddle under motor control.

Additionally illustratively according to this aspect of the invention, passing an ultrasound beam having a frequency greater than 3 MHz, preferably about 5 MHz or more, through the paddle and the compressed breast tissue includes passing an ultrasound beam having a frequency greater than 3 MHz, preferably about 5 MHz or more, generated by a linear array ultrasound transducer through the paddle and the compressed breast tissue in direct contact with the paddle.

Illustratively according to this aspect of the invention, passing an ultrasound beam having a frequency greater than 3 MHz, preferably about 5 MHz or more, through the paddle and the compressed breast tissue includes scanning an ultrasound transducer across a surface of the paddle opposite the surface of the paddle in contact with the compressed breast.

Further illustratively according to this aspect of the invention, scanning an ultrasound transducer across a surface of the paddle includes manually scanning an ultrasound transducer across a surface of the paddle.

Alternatively illustratively according to this aspect of the invention, scanning an ultrasound transducer across a surface of the paddle includes automatically scanning an ultrasound transducer across a surface of the paddle.

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Figure 1:
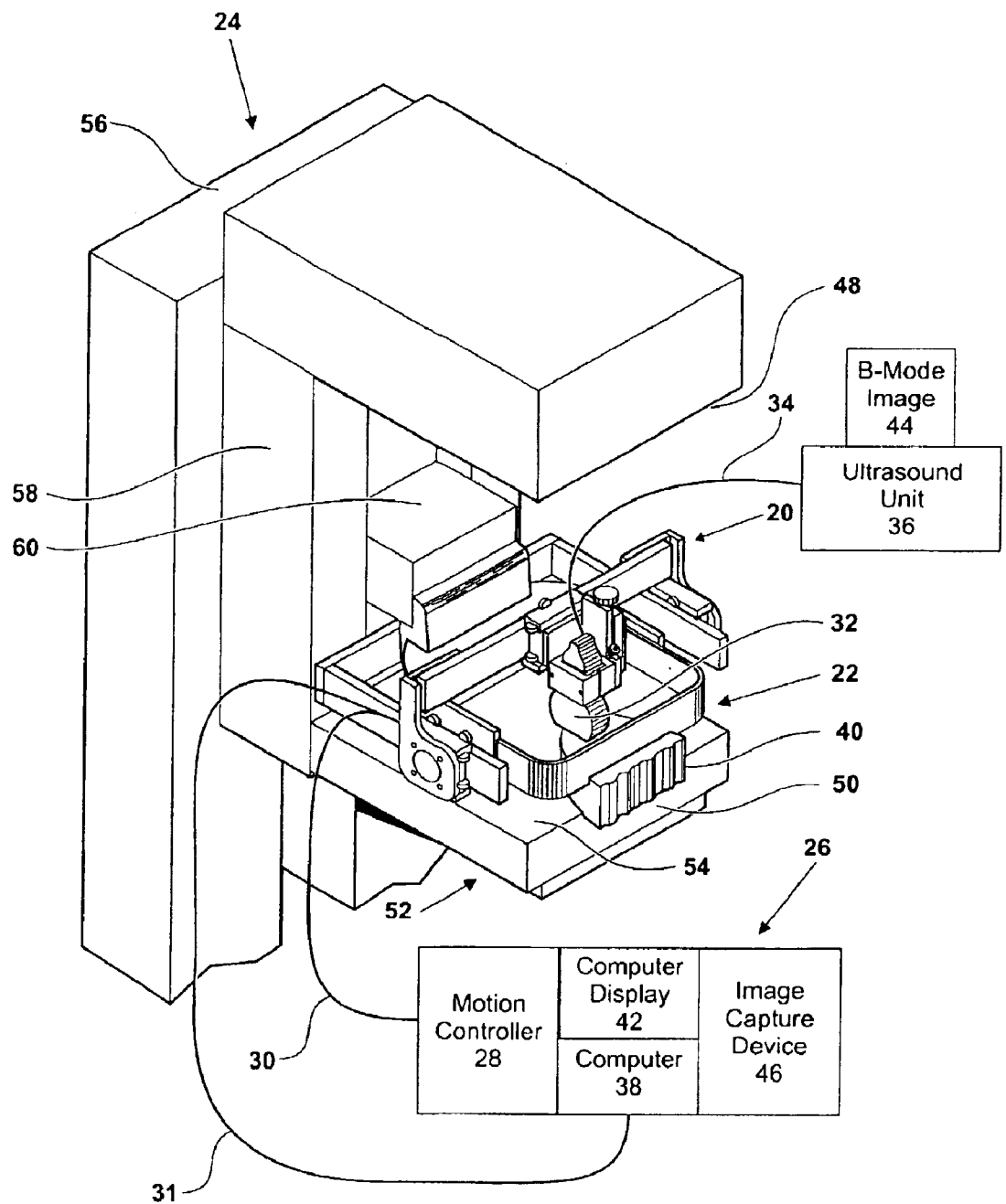
FIG. 1 illustrates a perspective view of a detachable, three-dimensional, computer-controlled XYZ mechanical scanner with an ultrasonic imaging unit and an x-ray mammography system, all according to the present invention.

FIG. 1 illustrates a combined ultrasound and x-ray imaging system according to the present invention, as applied to multi-modal diagnostic breast imaging. The illustrated embodiment adapts medically-accepted, FDA-approved, ultrasound linear array imaging systems, x-ray mammography units, and compression paddles to realize a diagnostic imaging modality for detection and assessment of breast cancer and other breast abnormalities. The modality combines two-dimensional x-ray imaging with three-dimensional ultrasound imaging, with the breast immobilized in the same configuration for both. Ultrasound and x-ray views of abnormalities are thus spatially registered, simplifying interpretation of breast masses.

A three-dimensional mechanical scanner 20 carries an x-ray mammography compression paddle assembly 22, which is, in turn, inserted into an x-ray mammography unit 24 such as, for example, a Lorad x-ray mammography machine. A computer control system 26 drives the motion systems of mechanical scanner 20, using a motion controller 28 via a motion controller cable 30, senses their positions, acquires two-dimensional ultrasound image data generated by a linear array probe 32 connected by a probe cable 34 to an ultrasound unit 36 such as, for example, Acoustic Imaging, Inc.'s Model 500S B-Mode Scanner, and a computer 38 constructs three-dimensional ultrasound views of the compressed breast 40 of a patient. The three-dimensional images are displayed on the computer display 42. Normal two-dimensional ultrasound (B-mode) images are displayed on a B-mode image display 44. These B-mode images are captured by an image capture device 46. The ultrasound views are in spatial registration with a standard x-ray image generated by x-ray mammography unit 24. The x-ray image is produced by electronics driving an x-ray tube 48 causing x-rays to be transmitted through compressed breast 40 to be received by a suitable x-ray image detector 50 within a detector assembly 52. The detector assembly 52 includes a lower compression plate 54, or surface, supporting the underside of compressed breast 40.

X-ray mammography unit 24 generally comprises a vertical x-ray support column 56 with a C-arm 58 movably attached, which, in turn, contains x-ray tube 48, a movable paddle mount block 60, and detector assembly 52. The mechanical scanner 20 is connected to compression paddle assembly 22, which is plugged into paddle mount block 60. Typically, C-arm 58 can be rotated in a plane parallel to the patient's chest wall and positioned vertically so patient's breast 40 can be inserted between compression paddle assembly 22 and lower compression plate 54 over a range of angular rotations. Force applied by movable paddle mount block 60 compresses the breast 40 under compression paddle assembly 22. The relationship of the overall imaging system with respect to the patient, or the views that can be realized, includes the standard mammography views: cranio-caudal, medio-lateral, and angles in between. Some additional ultrasound images are also possible.

Figure 2A:
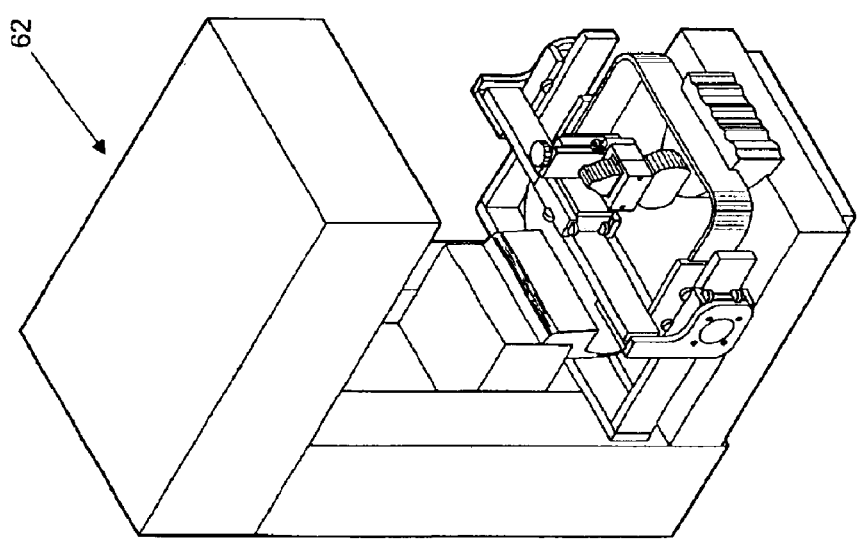
FIG. 2A illustrates a cranio-caudal view of an embodiment of the present invention.
Figure 2B:
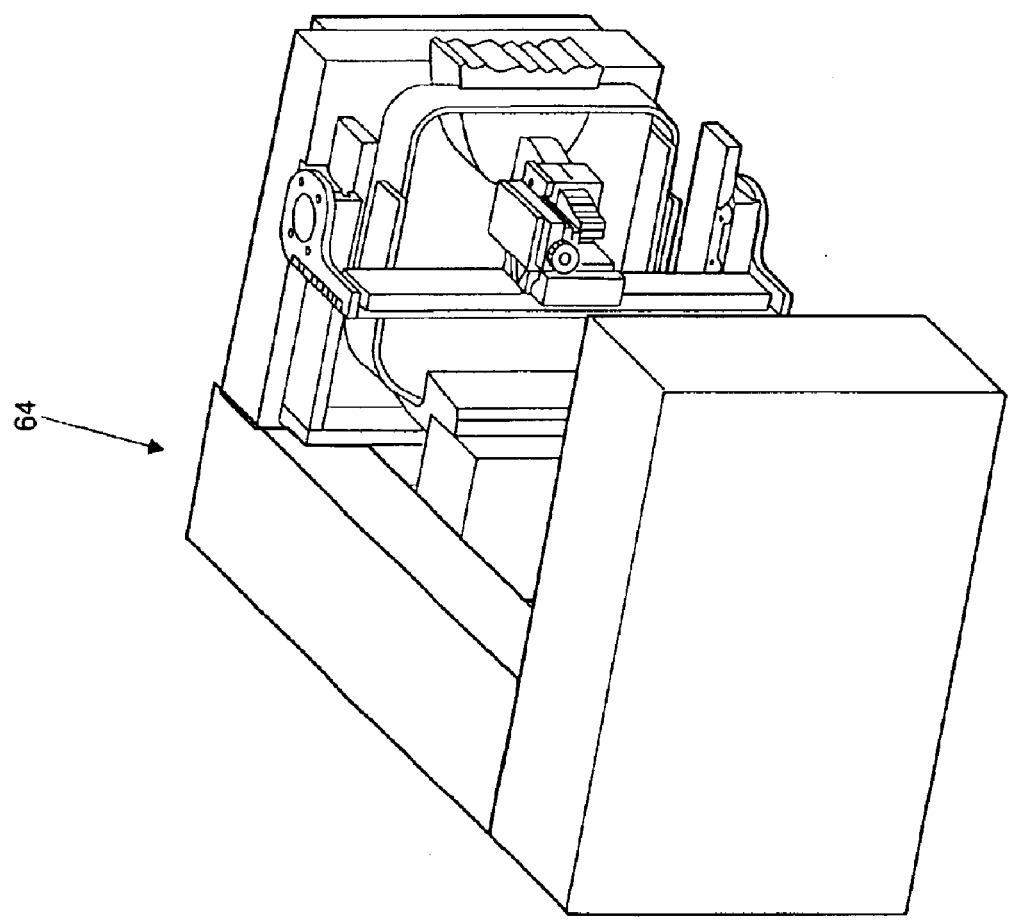
FIG. 2B illustrates a medio-lateral view of an embodiment of the present invention.
Figure 2C:
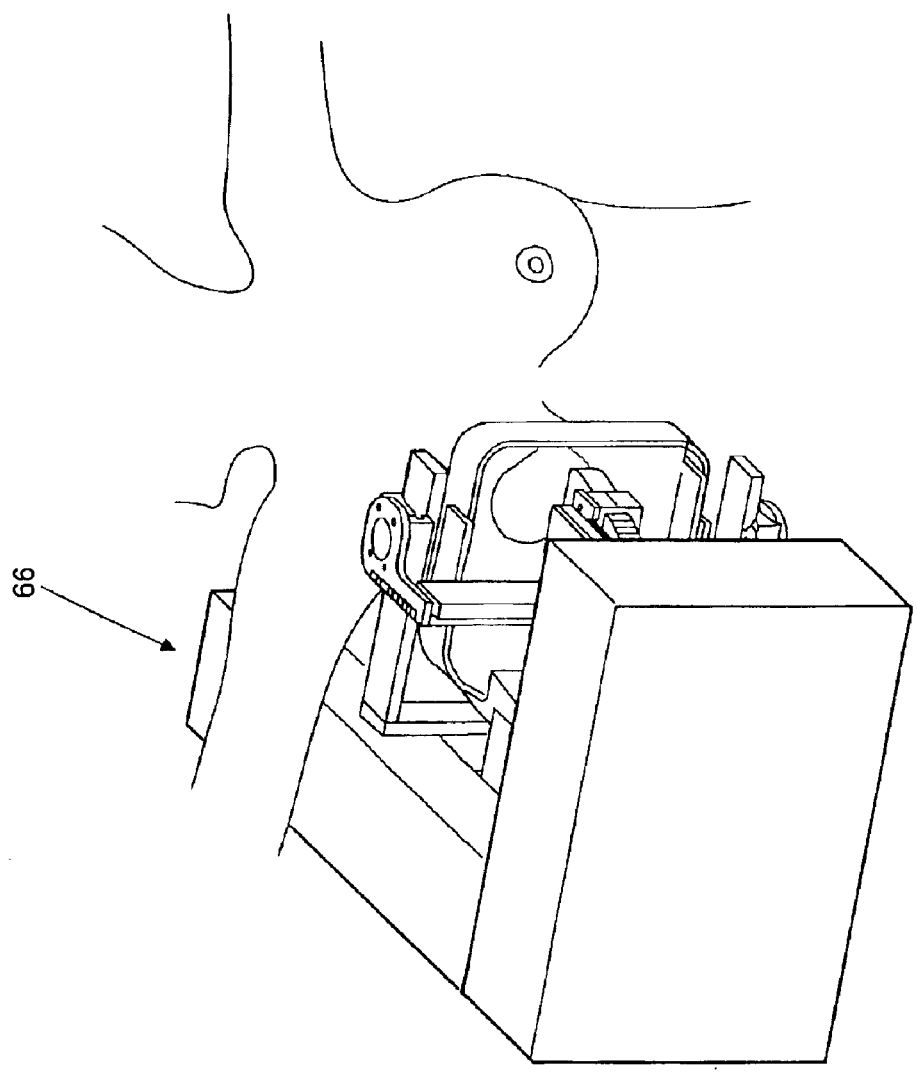
FIG. 2C illustrates a head-on view of an embodiment of the present invention.

FIG. 1 illustrates the orientation for a cranio-caudal (head-to-foot) radiographic view. In this view, both the through-transmission and echographic volume ultrasound image can be obtained. Rotating the C-arm 58 by 90 degrees counter clockwise on the support column 56, in a plane parallel to the chest wall, the operator can orient the breast 40 for a medio-lateral or latero-medial view (middle-to-side, or side-to-middle). In these views, as in the cranio-caudal view, x-ray and two-dimensional ultrasound images can be obtained in registration. Though x-ray mammography is a well-accepted imaging modality for breast cancer detection, it has several shortcomings. First of all, only a through-transmission image related to integrated tissue density is obtained. Overlying diagnostic features are summed together, resulting in the possibility that important information is blurred, summed, and overlaid so it cannot be detected in the x-ray image. A further shortcoming is that the breast is imaged only up to the chest wall, but there may be abnormalities further that are not recorded on the x-ray film. The present invention provides an additional imaging view particularly appropriate for this latter situation. If the paddle mount block 60 is translated far enough to provide enough room for the patient's body to fit between compression paddle assembly 22 and detector assembly 52, then the patient can stand between these, facing the paddle, when the overall system is rotated into the head-on view. In this orientation, the patient can either lean against the paddle or, under motor control, the paddle can contact the breast while the XYZ scanner 20 performs a scan. The resulting three-dimensional ultrasound image then visualizes features from the nipple into the chest wall to better examine regions that are inaccessible to standard mammography. This is the "head-on" position. The illustrated embodiment is capable of producing, among others, the scans illustrated in FIG. 2A, FIG. 2B, and FIG. 2C namely, cranio-caudal view 62, illustrated in FIG. 2A, medio-lateral view 64 illustrated in FIG. 2B, and head-on view 66 illustrated in FIG. 2C.

Figure 3:
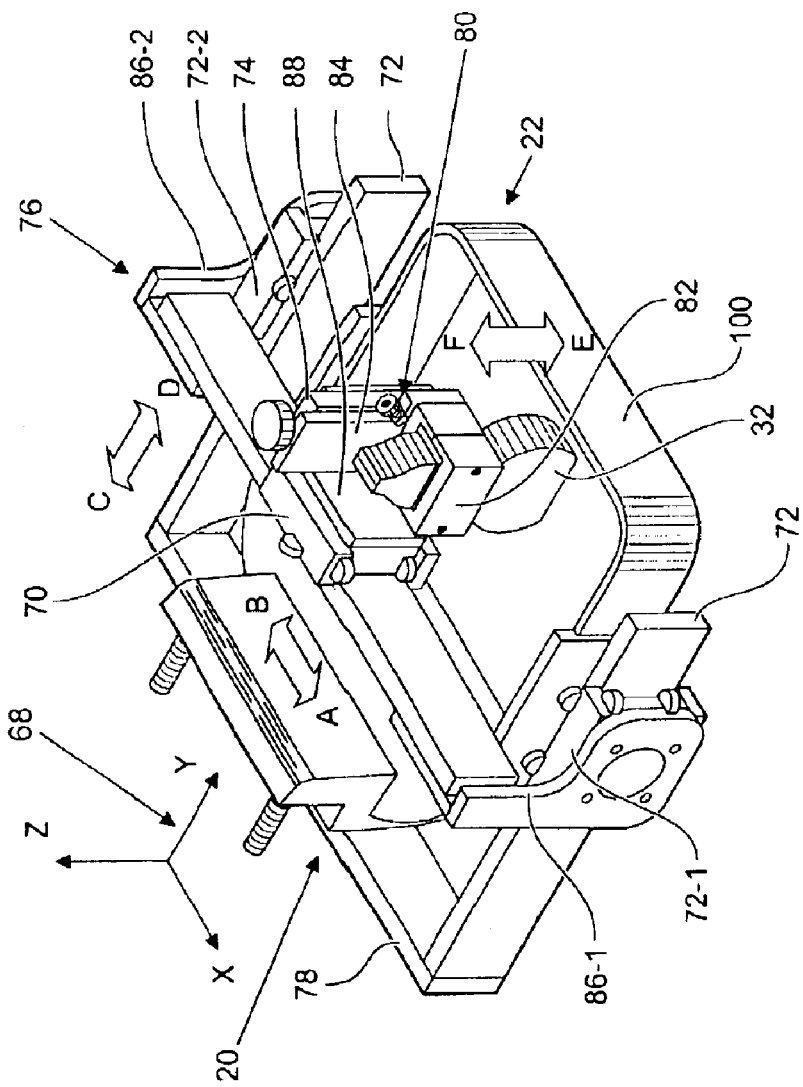
FIG. 3 illustrates a perspective view of the mechanical scanner with a compression paddle inserted.

Generally, as illustrated in FIGS. 1 and 3, the system comprises a three-dimensional mechanical positioning system for scanning, under computer 38 control, an ultrasonic linear array probe 32 across an immobilized breast 40 to yield a three-dimensional image registered to a spatial XYZ coordinate frame 68 such as the frame illustrated in FIG. 3. Such coordinate frames establish direction references oriented as illustrated in FIG. 3 for discussion, for mathematical convenience, and by convention, but the origins of such frames clearly can be fixed at arbitrary points in three-dimensional space. Referring further to FIG. 3, mechanical scanner 20 positions linear array probe 32 using an X-axis actuator 70, Y-axis actuators 72-1 and 72-2, and a Z-axis positioner 74. Y-axis actuators 72-1 and 72-2, comprising left Y-axis actuator 72-1 and right Y-axis actuator 72-2, are attached in parallel to support bar 78, forming a rigid frame for overall support. Typically, left Y-axis actuator 72-1 and right Y-axis actuator 72-2 are identical, except for orientation, and are operated in parallel, while the X-axis actuator 70 may be the same as Y-axis actuators 72-1 and 72-2 with the possible exception of its length. The X-axis actuator 70 is mounted across Y-axis actuators 72-1 and 72-2, forming XY positioner 76. This combination provides planar positioning for the attached Z-axis positioner 74 carrying probe assembly 80. The probe assembly 80 integrates linear array probe 32, a probe jacket 82, and a probe mount plate 84. The ultrasonic linear array probe 32, mounted in probe assembly 80, is attached to, and is positioned vertically by Z-axis positioner 74 to complete a three-dimensional XYZ scanning mechanism. The X-axis actuator 70 is mounted to left Y-axis actuator 72-1 and right Y-axis actuator 72-2 by left XY plate 86-1 and right XY plate 86-2 respectively. The Z-axis positioner 74 is mounted to the X-axis actuator 70 by an L-shaped XZ plate 88.

Figure 4:
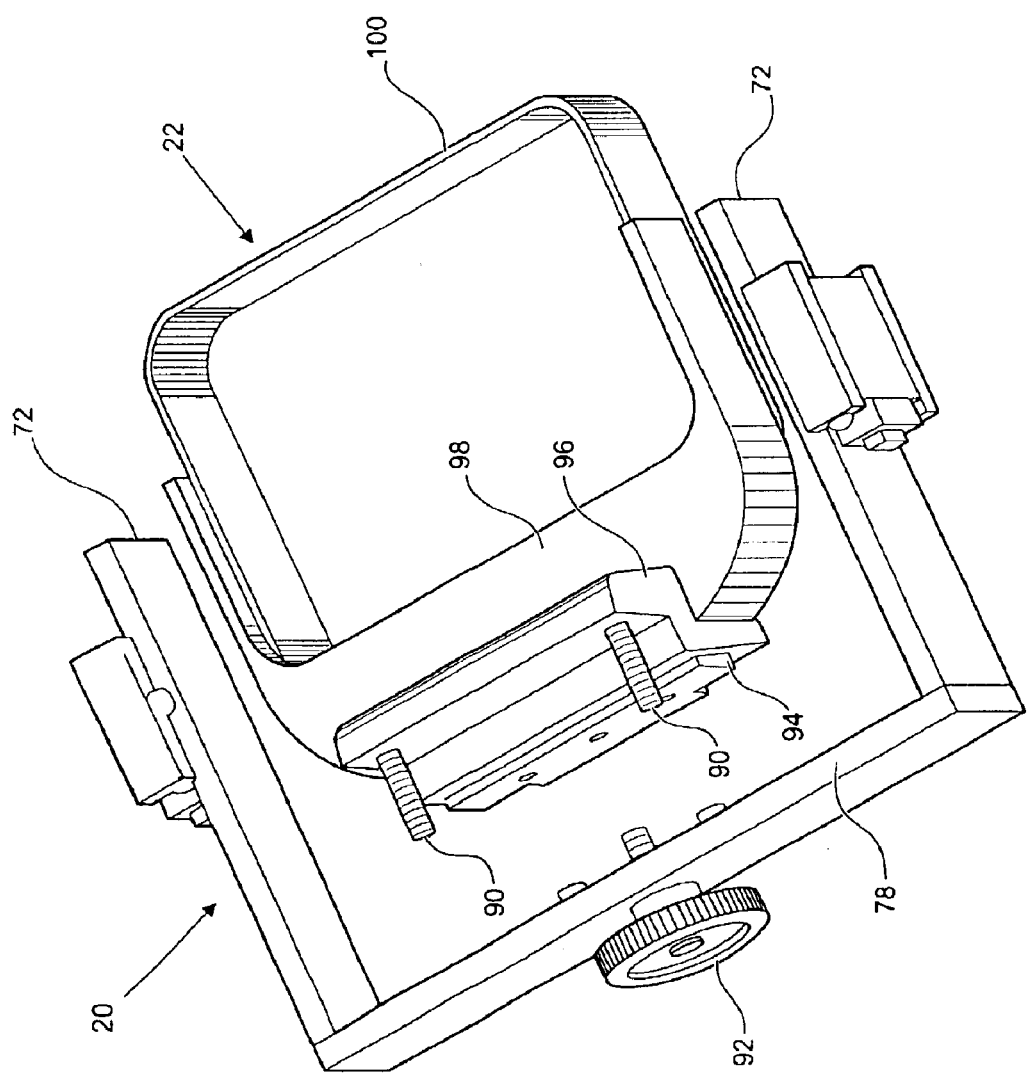
FIG. 4 illustrates connection of the mechanical scanner to a paddle assembly.

Referring now to FIG. 4, compression paddle assembly 22 is fitted between Y-axis actuators 72-1 and 72-2, aligned to support bar 78 by a paddle bracket guide pin 90 and secured to support bar 78 by a captive screw 92. The captive screw 92 engages a threaded paddle adapter plate 94 attached to paddle bracket 96 supporting a paddle yoke 98 with an attached plastic paddle 100. Although FIG. 4 illustrates the paddle 100 as being inserted into mechanical scanner 20 with some parts removed, in practice the paddle 100 can be inserted without any disassembly. It can be angled into place from below. Paddle 100 can be constructed from, for example, Lexan® polycarbonate plastic.

One of the aspects of the invention is the development of experience with various materials for paddle 100. Specifically, plastics were investigated to determine ones which were appropriate for breast compression paddles 100. Our research has demonstrated that, while certain materials such as plexiglas attenuate ultrasound to a lesser degree than others, for example, polycarbonates, their other physical characteristics are not as advantageous for breast compression as polycarbonates. Since both x-ray and ultrasound attenuation are dependent on the thickness of the paddle 100 material, we investigated decreasing the thickness of the paddles 100 from thicknesses known in the prior art, for example, 0.12 inch (about 3 mm), while maintaining safety and ensuring that standard x-ray mammography pressures could be applied with these thinner materials. Compression paddles 100 were constructed from various types of plastics using thicknesses of 0.02 inch (about 0.5 mm), 0.04 inch (about 1 mm), 0.06 inch (about 1.5 mm), 0.08 inch (about 2 mm), and 0.12 inch (about 3 mm). These paddles 100 were evaluated in terms of their ability to permit transfer of high frequency ultrasound while meeting the required standards for breast compression paddles. One result of our investigations was the finding that, with use of current ultrasound breast imaging systems, ultrasound with a frequency of 7.5 MHz can be transmitted across a polycarbonate compression paddle with a thickness of 0.12 inch (about 3 mm). These investigations also demonstrated that it is possible to design breast compression paddles from various plastics, such as polycarbonate, which are thinner than those previously used for x-ray mammography while permitting application of standard breast compression pressures. By decreasing the thickness of the paddle material, the ultrasound attenuation is decreased and thus higher ultrasound frequencies can be applied. Ultrasound frequencies of 13 MHz were used to examine patients in the standard craniocaudal compressed breast position. The polycarbonate paddles 100 designed and fabricated for those investigations had a thickness of 0.04 inch (about 1 mm). Additional investigations indicated that frequencies as high as 20 MHz can be transmitted through appropriately designed polycarbonate compression paddles. These findings are significant. A standard x-ray mammography compression paddle can be used when 3D ultrasound imaging is performed using frequencies in the range of, for example, 7.5 MHz to 10 MHz. If it is desired to use higher frequencies, appropriately thinner paddles can be used.

It is generally recognized in the medical community that x-ray mammography is diagnostically beneficial and appropriate for routine examination of subjects age 40 and older, and generally for any age adult with evidence of possible pathology, such as palpable breast mass or other overt symptom. For subjects under 40 with no symptoms of pathology, it is recommended that these individuals carry out routine self-examination and, at intervals, undergo a hand-applied breast palpation examination performed by a physician. X-ray examination is not recommended as a routine screening method for young, asymptomatic patients because of the possibly long-term deleterious effects of exposure to ionizing radiation. In addition, in comparison to results achieved with older subjects, x-rays are less effective in detecting pathologies in the normally dense breast tissue of young individuals.

Masses detected by hand breast palpation are generally of the order of 1 cm or more in size. At the time of detection, a large sized malignant mass may be accompanied by metastases to other breast or body regions. The presence of (a) large tumor(s) may require a mastectomy rather than surgical removal of the mass and some surrounding tissue. Life span following detection of breast cancer is related to the size of the mass and its treatment at the time of detection. For young subjects, there is a current need for development of non-ionizing breast examination instruments which can improve the detection of small breast masses or other subtle indications of the presence of breast cancers. It is medically accepted that ultrasound imaging is non-injurious and, compared to x-ray imaging, is more effective in imaging the dense breast tissue of young subjects.

With the exception of Japanese physicians, ultrasound imaging is not generally accepted as a breast screening method for either young or older subjects. The variable results obtained at different medical facilities using current ultrasound imaging techniques to examine the whole breast constitute the primary basis for this lack of acceptance. Detection of a small mass in an unknown breast area by application of an ultrasound transducer in contact with a freely movable unencumbered breast is critically dependent on the technical training of the individual carrying out the examination. Specific knowledge is required on basic mechanisms involved in the interaction of ultrasound with soft tissue and an awareness of possible false imaging data associated with an inadequate examination technique. In the United States, technologists generally carry out the ultrasound breast examinations. A solution to this long-term problem is to design an ultrasound examination system which is machine-based, automatic and capable of improving the detection of small breast masses in asymptomatic subjects by the use of higher ultrasound frequencies than are applied in the prior art. The compression paddle knowledge developed during the course of this investigation provides an automated high-frequency ultrasound imaging system for breast examination of young, asymptomatic patients. In the design of this instrumentation system, the subject can either be standing or sitting and a compression paddle capable of transmitting high frequency ultrasound contacts the entire anterior surface of the breast, the head-on position. Under motor control, the breast is compressed by the paddle. This motorized compression decreases the depth of the breast tissue which must be traversed by the ultrasound, thus permitting the use of higher ultrasound frequencies with their attendant higher resolution capability. A high frequency linear array ultrasound transducer in direct contact with the paddle, using an appropriate coupling medium as necessary, scans all areas of the breast by means of automated linear translation. Patient examinations have been conducted successfully in this head-on orientation using the paddles of both Bennett and Lorad x-ray mammography systems to apply the pressure to compress the breast. In these examinations, the ultrasound transducer was scanned manually. It is contemplated that the ultrasound transducer would also be rotated automatically around the nipple-areolar region to image the ductal structure, a region where breast cancer may initially be evident.

The availability of such high frequency, automated ultrasound examination systems is of particular importance for improving detection of pathologies in the breasts of asymptomatic young subjects. The availability of high frequency ultrasound not only increases resolution, but also improves detection of microcalcifications, a significant indicator of possible breast cancer. In the prior art, x-ray mammography is the best technique for detecting microcalcifications. However, as previously noted, x-ray mammography is not the preferred modality for asymptomatic young patients, and so the higher resolution offered by higher frequency ultrasound offers another mechanism for the detection of microcalcifications in asymptomatic young patients.

Ultrasound scanning in the head-on position using an ultrasound-transparent compression paddle offers numerous advantages including very rapid whole breast imaging suitable for breast screening. Additionally, the patient is in a reasonably comfortable standing or sitting position. Using relatively higher ultrasound frequencies, resolution is sufficiently high to detect microcalcifications previously only detectable by x-ray imaging. Use of the compression paddle to reduce the thickness of the tissue the ultrasound must traverse permits the use of these relatively higher frequencies. Automated pressure application to the breast in the head-on position can help differentiate the characteristics of cystic and solid masses. A head-on automated machine can be applied both to produce a two-dimensional B-mode scan, and to produce the 3D images of the method and apparatus which form a part of this invention.

Figure 5:
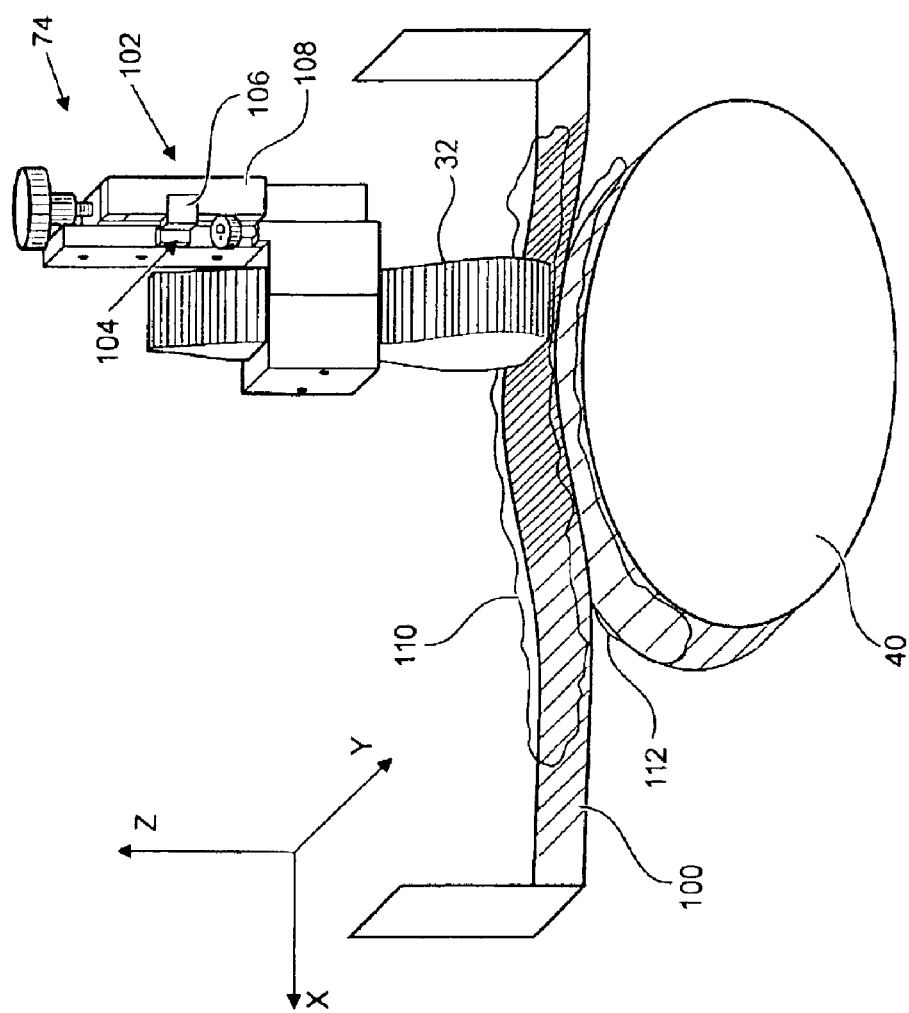
FIG. 5 illustrates a plastic paddle deflected by a compressed breast.

Referring to FIG. 5, linear array probe 32 is scanned across plastic paddle 100 by the XY positioner 76, and is permitted to follow its possibly curved contour. The plastic paddle 100 may be deflected in the +Z direction during use by compressed breast 40. Deflection as detected by Z-axis position encoder 102 serves as an input to software executed by the computer 38 (See FIG. 1) for use in three-dimensional image construction. The Z-axis position encoder 102 including encoder linkage 104, linear encoder sensor 106, and linear encoder graticule 108, monitors the Z-position of probe assembly (See FIG. 3).

In FIG. 5 it will be noted that probe 32-to-paddle 100 couplant 110 and paddle 100-to-breast 40 couplant 112 are used during scanning to couple the ultrasonic waves acoustically to the breast 40 tissue. In order for ultrasonic waves to propagate into the breast 40, be reflected by tissue interfaces within the breast 40, and be received by the probe 32, it is necessary to use a coupling gel or other coupling material on the top surface of the paddle 100 (probe 32-to-paddle 100 couplant 110). A couplant is also required between the underside of the paddle 100 and the breast 40 (paddle 100-to-breast 40 couplant 112). As illustrated in FIG. 5, compression of the breast 40 generally results in deflection of the paddle to form a curved contour. The Z-axis assembly presses the probe 32 against the top surface of the paddle 100, while the x-ray unit vertical axis presses the paddle 100 to the breast 40. The Z-axis positioner 74 thus presses the probe 32 into the layer of coupling material 110 to maintain acoustic wave coupling and effective propagation of waves.

Figure 6A:
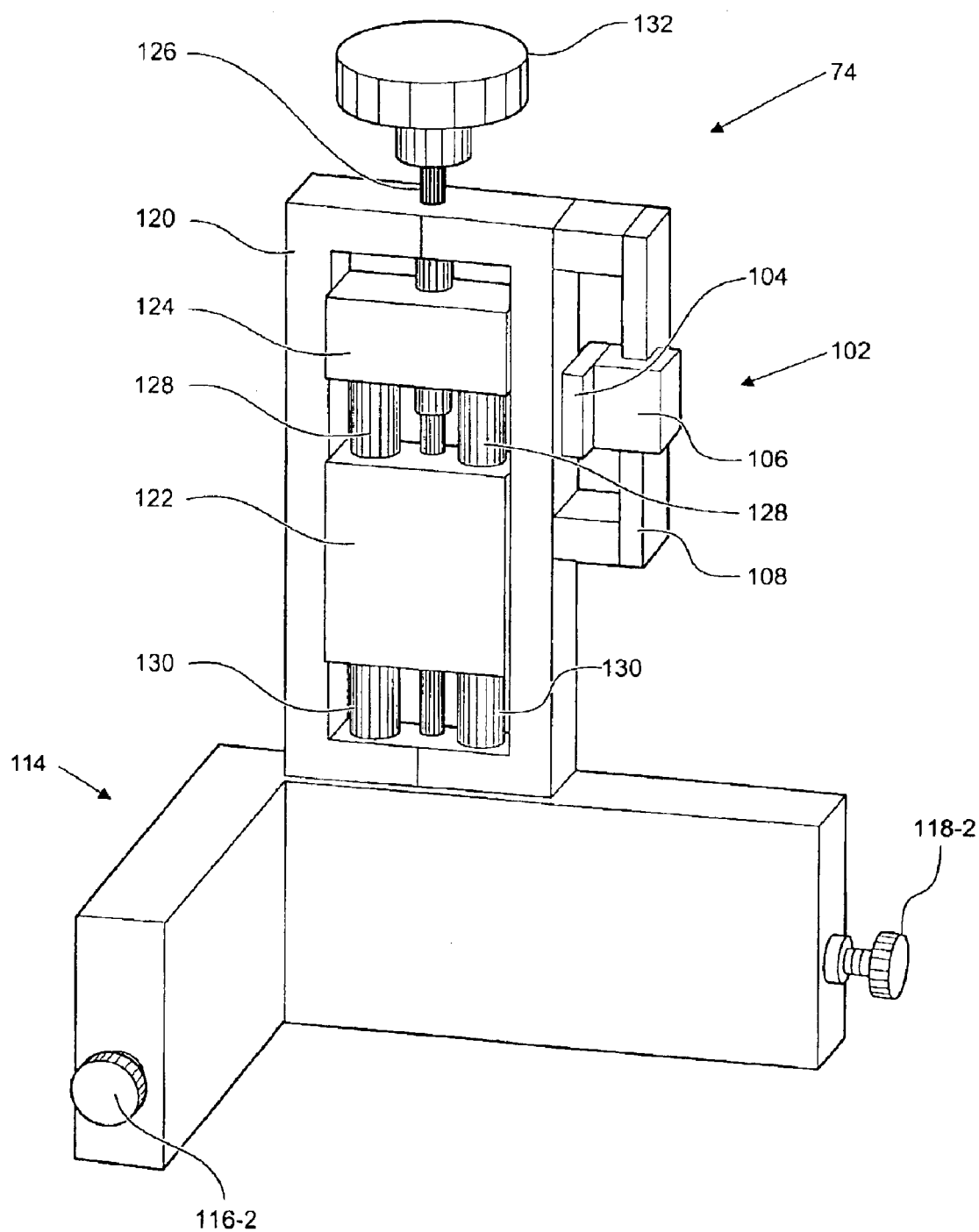
FIG. 6A and FIG. 6B illustrate details of a Z-axis positioner.
Figure 6B:
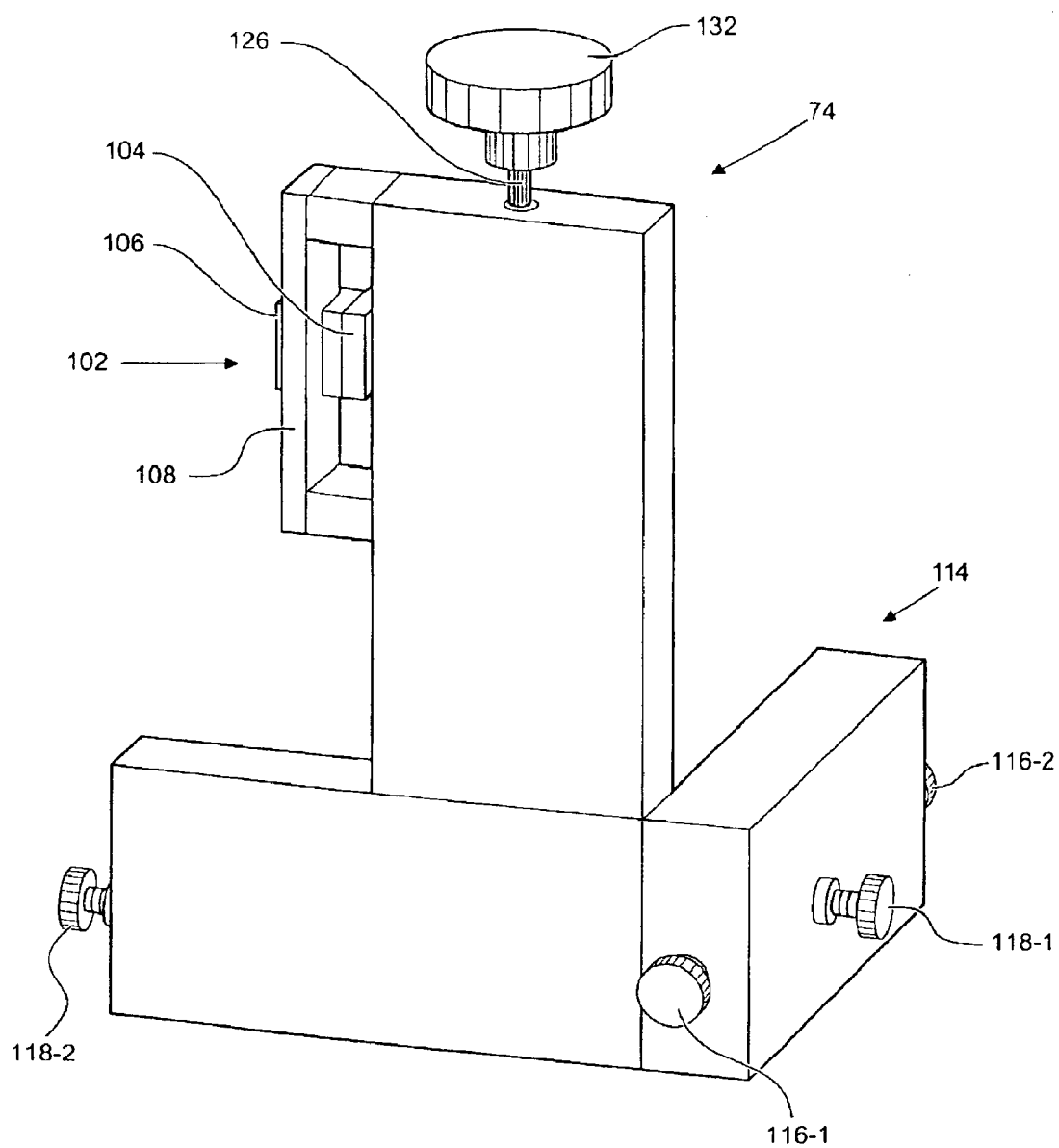

In FIGS. 6A and 6B, limit switches 114, X-axis lower limit switch 116-1, X-axis upper limit switch 116-2, Y-axis lower limit switch 118-1 and Y-axis upper limit switch 118-2, are monitored by a motion controller 28 (FIG. 1) to determine automatically the maximum X-Y scan extent of inserted plastic paddle 100. Therefore, various sized standard paddles 100, after modifications for mounting, can thus be effectively employed for various-sized breasts 40, and their size can be detected automatically.

Further detailing the Z-axis functions in FIGS. 6A and 6B, there are several ways to maintain probe 32 contact. In the illustrated embodiment, this is accomplished using a spring-loaded, floating mount block on the Z-axis to which is attached the probe mount assembly. Referring to FIG. 6A, Z-axis positioner 74 includes a dovetail base 120, wherein a suspended block 122 and a contact force block 124 can move in the Z direction. A Z-axis shaft 126 passes through both blocks. Z-axis shaft 126 is threaded over the travel limits, including throughout the range of the contact force block 124 and extending above and below contact force block 124 to yield about 0.5 in. of vertical travel. Z-axis shaft 126's threads engage contact force block 124 to apply force via upper suspension springs 128 to suspended block 122, which is suspended from below by lower suspension springs 130. The arrangement provides for adjustment of the probe 32-to-paddle 100 contact force via a contact force adjuster 132.

Figure 7:
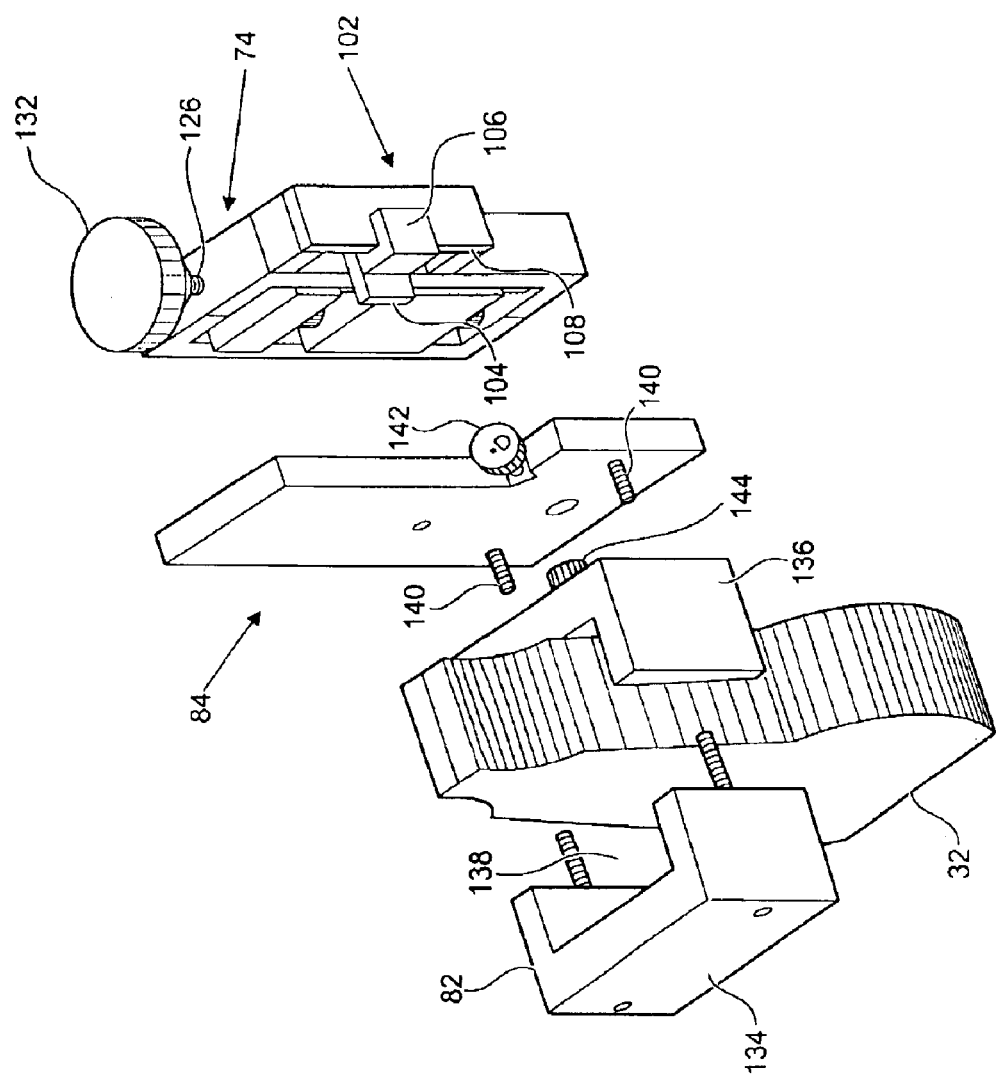
FIG. 7 illustrates an exploded view of a Z-axis positioner and probe assembly.

In FIG. 7, a probe mount plate 84 carries an encoder linkage 104 to move linear encoder sensor 106 along linear encoder graticule 108 to track the vertical (Z) position of the probe 32 via an electrical connection between a Z-axis position encoder 102 and motion controller 28 (FIG. 1).

Unlike previous two-dimensional scan systems of the general types described in, for example, U.S. Pat. Nos. 5,474,072; 5,479,927; 5,640,956; 5,664,573; and, 5,938,613, Z-axis positioner 74 permits the probe 32 to "float" or ride along the contour of an upwardly curved plastic paddle 100 as deflected by compressed breast 40 (FIG. 5). Since the Z position is sensed as the scan proceeds, the vertical positions of two-dimensional images, as generated by ultrasound unit 36, are known and can be used to perform spatially accurate, three-dimensional image construction. If the probe 32 is fixed in its Z position, as it is in, for example, U.S. Pat. Nos. 5,474,072; 5,479,927; 5,640,956; 5,664,573; and, 5,938,613, then the flexible plastic paddle 100 will be pushed downward against the breast 40 as images are acquired, distorting the soft tissue as it passes, thus losing the registration of adjacent image planes with respect to each other in the Z direction. Subsequent construction (combination, merging, interpolation) of these misaligned planes into a three-dimensional image will result in inaccurate construction of breast 40 features. A typical ultrasound linear array system operating at 7.5 MHz has a resolution of about one to two wavelengths (about 0.2 mm to about 0.4 mm) in the B-mode plane. Thus, if the paddle 100 is deflected upwardly, curved, or bent by, on the order of 0.2 mm to 0.4 mm, the inherent resolution provided by a prior art ultrasound unit may be lost, thereby compromising the clinical acceptability of the whole approach. Errors introduced by ignoring a curved paddle would be relatively larger at higher frequencies. Thinner paddles are desirable because they permit higher ultrasonic frequencies to be used, resulting in higher resolution. However, curvature of the paddles is more pronounced as the paddles become thinner. The encoded Z axis permits this curvature of thinner paddles to be accommodated.

The present system is designed to accept linear array probes 32 from a variety of manufacturers to realize the goal of a versatile adapter for three-dimensional imaging. As best illustrated in FIG. 7, a mechanical adapter probe jacket 82 adapts a given probe 32 for mounting to a probe mount plate 84. The probe jacket 82 is a split plastic block including a front block 134 and a rear block 136 forming a clamp around the probe 32 handle, as secured by screws. A probe jacket aperture 138 in the split block is formed, for example, by machining, to fit the probe handle. This permits probes 32 that are designed for hand-held operation to be used by the three-dimensional scanner, thus extending the utility of standard linear array scanners. The present invention can be adapted to most ultrasound units, so that it can be used as an "add on" enhancement to existing ultrasound systems, to extend the imaging capability of such systems to three dimensions. The probe jacket 82, carrying linear array probe 32, is guided onto probe mount plate 84 by probe mount plate guide pins 140 and secured by a probe mount plate set screw 142 tightened against a probe latching pin 144. Merely loosening probe mount plate set screw 142 permits removal of the combined probe jacket 82 and probe 32. The probe 32 can be removed, for example, to eliminate it from the x-ray field of view when small compression paddles 100 are used for spot imaging. Several probes 32, perhaps with different center frequencies and sizes, are typically provided with standard ultrasound breast images. The probe assembly mount design is meant to make it convenient to change probes 32 rapidly while maintaining accurate positioning and probe 32 orientation.

The computer control system 26 illustrated in FIG. 1 is interfaced to the overall XYZ assembly by wiring 30 for programmed motion in X and Y directions and sensing of the XYZ position of linear array probe 32, and by interface 31 for acquisition, construction and display of spatially registered ultrasound and x-ray images. The computer display 42 is provided for user operation of the system, via a graphical user interface, for monitoring, controlling, and displaying the position of various positional assemblies, initiating diagnostic scans, recalling previous scans, displaying two and three-dimensional images, and storing results.

Figure 8:
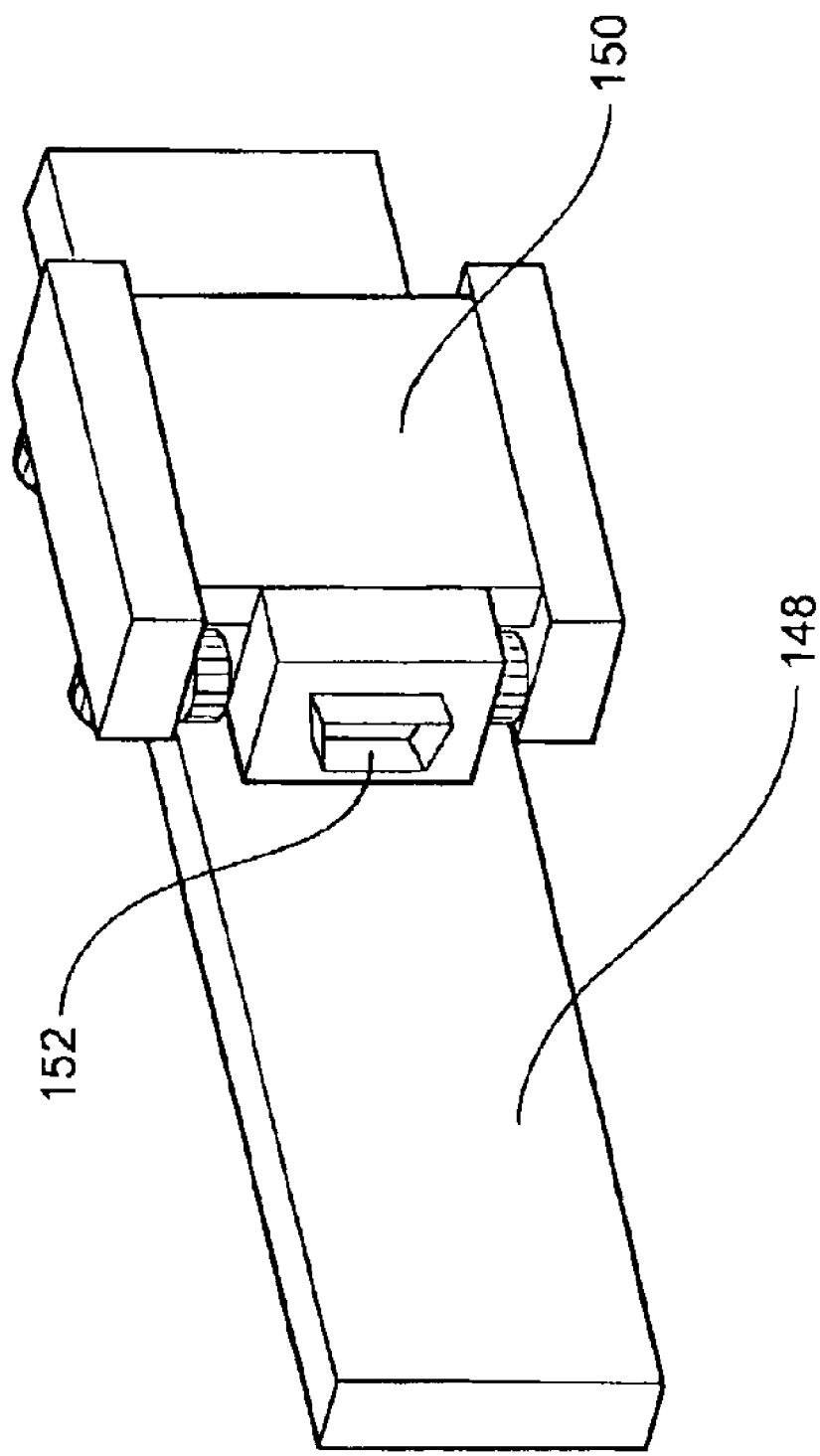
FIG. 8 illustrates a linear stepper motor.

In the illustrated embodiment, the X and Y actuators are linear stepper motors of the general type available from, for example, Northern Magnetic, Inc., 25026 Ana Drive, Santa Clara, Calif. 91355. A linear stepper motor 146, as illustrated in FIG. 8, includes a platen 148 and a forcer 150 with a motor electrical connector 152. A linear electric motor can be thought of as a rotary electric motor that has been cut along the radial plane and unrolled. The resultant motor is capable of producing a linear thrust. Although perhaps not as common as rotary motors, linear motors offer several distinct advantages. First, the platens 148 can be used to form part of the frame (support) of the scanner, thereby resulting in a more compact design while reducing overall complexity. In the illustrated embodiment, this permits the mechanical scanner 20 to remain attached to the x-ray mammography unit 24 while x-ray imaging is performed without interfering with image formation. This eliminates the need for complicated swing-away or hinged mechanisms to move the mechanical scanner 20 out of the x-ray field of view. The patient can remain in the same position for both the x-ray and the ultrasound examinations, permitting the operator to register the x-ray and ultrasound images spatially, thereby facilitating the interpretation of breast 40 abnormalities. Linear motors are direct drive mechanisms, thereby eliminating backlash inherent with lead screws, ball screws, belt drives, rack and pinion mechanisms, and the like. In the illustrated embodiment, two-way, or raster, scanning can be performed without an encoder, while still maintaining high position accuracy without the need for backlash compensation. A more robust, rapid, and simple system results. Linear motors offer further advantages, including improved reliability, a wide range of velocities, smoothness, accuracy, stiffness, and increased overall life expectancy. A linear motor suitable for the present application is available from Northern Magnetic as Model 1302, which produces 5 pounds of force. A larger motor or counterweight may be necessary for smooth operation when the scanner is oriented with the X axis vertical.

In operation, the illustrated embodiment performs multimodal x-ray and three-dimensional ultrasound imaging of a breast 40 under compression. A typical patient examination is performed as follows. A suitable compression paddle assembly 22 is chosen according to the size of breast 40 to be imaged, is installed into mechanical scanner 20 (FIG. 3) and secured as illustrated in FIG. 4.

The scan adapter with mounted paddle 100 is plugged into x-ray mammography unit 24 using the standard left paddle assembly mount pin 156-1 and right paddle assembly mount pin 156-2. The resulting patient examination configuration presented to the medical practitioner is very similar to the standard x-ray mammography setup, except that mechanical scanner 20 surrounds compression paddle assembly 22 and carries linear array probe 32 above paddle 100. An interface cable carrying power and control signals is connected from mechanical scanner 20 to motion controller 28. Video output and synchronizing signals of ultrasound unit 36 in any suitable format, for example, NTSC, are connected to image capture device 46 via, for example, coaxial, video cabling. The image capture device 46 is typically a circuit card, for example, a Data Translation, Inc., Model 1352 capture card, plugged into the bus of computer control system 26. The computer control system 26 can be, for example, a personal computer (PC), such as, for example, an IBM Aptiva Model X computer, running a Microsoft Windows operating system, for example, Windows 98 or NT.

Once the overall mechanical adapter, x-ray unit, ultrasound unit, and compression paddle configuration is installed and interconnected, the patient examination can proceed. It will be understood that such setup, once completed, need not be repeated for subsequent patients. The illustrated embodiment can be left in place (installed, set up) without interfering with standard x-ray mammography procedures. This is important, since accepted medical practice and FDA-approved systems must not be compromised for the illustrated embodiment to be practical and efficacious.

The patient is prepared as if for a normal x-ray mammography examination, except that paddle 100-to-breast 40 couplant 112 is applied to the breast 40 prior to immobilizing the breast 40 under the x-ray compression paddle. The couplant 112 must not interfere with diagnostic features in the x-ray image. Since an x-ray mammogram displays the integrated density of the object through which it is transmitted, paddle 100-to-breast 40 couplant 112 that is too thick, or too dense, such that it, or its boundary, overlays (appears in) the breast 40 image features, would be unacceptable. Examples of suitable paddle 100-to-breast 40 couplant 112 include, for example, mineral oil, Jojoba oil, very thin layers of standard coupling gels, such as Aquasonic 100 coupling gel available from Parker Laboratories, Orange, N.J., and water. Compression of the breast 40 and configuration of the patient with respect to the x-ray unit are performed as for a normal x-ray examination.

The x-ray mammogram is obtained in the standard manner. During x-ray imaging, the XY positioner 76 carrying Z-axis positioner 74 and probe assembly 80 is moved away from the patent's chest wall to the back right (or left) corner of the XY scan extent. If necessary, the probe 32 with its probe jacket 82 is removed from mechanical scanner 20 so that no interference with the incident x-ray beam occurs.

Three-dimensional ultrasound imaging is performed after the x-ray. The probe 32-to-paddle 100 couplant 110 is applied after the x-ray image is obtained, and therefore can have no effect on the x-ray image. Suitable probe 32-to-paddle 100 couplants 110 include, for example, shallow water baths, coupling gel of any thickness, a layer of oil, cream, or other spreadable material affording ultrasonic wave coupling between probe 32 and paddle 100. The thickness or density of probe 32-to-paddle 100 couplant 110 is not as critical as for the paddle 100-to-breast 40 couplant 112 since, by the time it is needed, the x-ray image has already been obtained. If another x-ray is needed after probe 32-to-paddle 100 couplant 110 has been applied, the couplant can cleaned from the paddle.

Ultrasonic scanning is performed after applying probe 32-to-paddle 100 couplant 110. The probe assembly 80 is mounted on the scanner 20, if not already present. Generally, the operator manually moves the probe 32 around over the paddle 100 and visualizes the breast 40 as in a normal ultrasound exam. When the current to the linear motors is turned off, the probe 32 can be freely moved by hand, and the breast 40 can be examined using standard ultrasonic breast imaging protocols. The two-dimensional (B-mode) image, as generated and displayed by ultrasound unit 36, is examined as manual scanning proceeds. When a region of interest is identified, the practitioner leaves the probe 32 at an XYZ position in that vicinity and initiates an automated scan.

Whether or not manual scanning is performed, an automated three-dimensional scan is initiated via a software graphical user interface residing on computer 38 (see FIG. 1). Referring to the XYZ coordinate frame 68 shown in FIG. 3, the linear array probe 32 is positioned in X and Y to a desired start position. The linear array probe 32 is swept in the +X direction while the video output of ultrasound unit 36 is digitized at a rate of N frames per second, where, for example, N=30. The X-axis actuator 70 is rapidly accelerated from rest (within 1 mm of travel), and the scan or sweep then proceeds at a constant velocity. Scan velocity is set via motion controller 28 to synchronize probe 32 position with image capture, such that images are digitized at multiples of a selected interval size along X, for example, 0.125 mm. The image sequence for each sweep in X is stored in computer 38 (See FIG. 1) memory, or on disk. The XY positioner 76 then shifts the probe 32 in the −Y direction, and another scan is performed along X as needed to cover the Y-extent of the desired breast region. The shift in −Y direction is typically set so that digitized, captured adjacent B-mode image planes will overlap from sweep to sweep. The overall XY scan motion and image capture can be a "raster" scan pattern, where the first sweep is in +X direction; shift in the −Y direction; the second sweep is in −X, back to the starting X; and so on, until the region is covered. Alternatively, image acquisition can be made to occur only on +X sweeps, where the probe 32 is returned to X start position before each shift in −Y.

If lead screw, rack and pinion, or other drive systems exhibiting backlash are used to implement the mechanical system, unidirectional scanning might provide greater accuracy. Use of linear stepper motors essentially eliminates backlash, so that a rapid and efficient raster scan can be reliably performed without the need for complex backlash correction schemes. The resulting minimization of total scan (image acquisition) time minimizes the time the breast 40 must be held under compression, and thus reduces patient discomfort. Total scan times experienced in a system constructed and operated according to the present invention were in the range of about 1 minute long.

Figure 9:
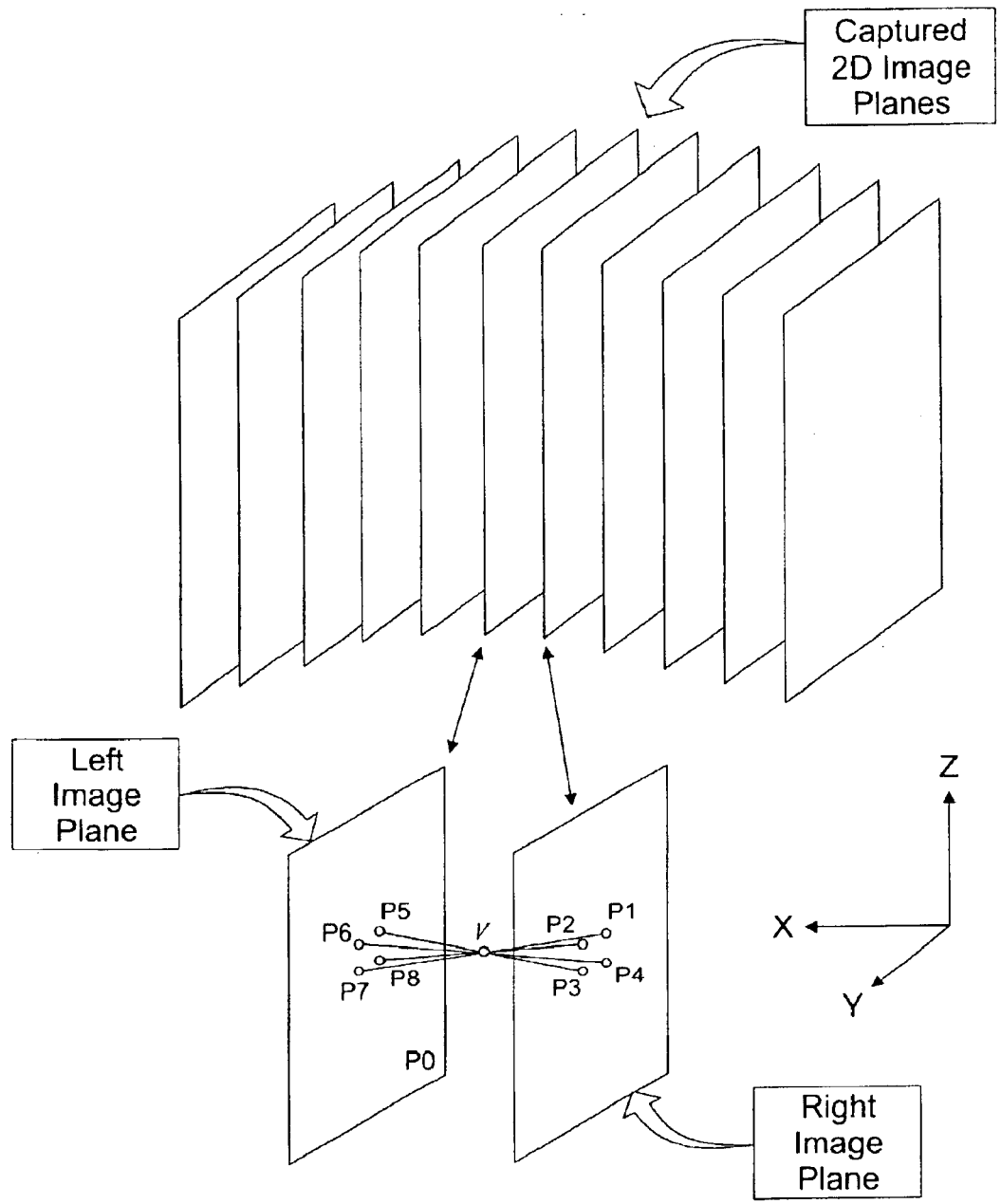
FIG. 9 illustrates three-dimensional interpolation in volumetric construction.

Once individual two-dimensional, overlapping image sequences are obtained, they are constructed by specialized software residing on computer 38 (See FIG. 1) into a three-dimensional volumetric image. Construction is illustrated in FIG. 9, and proceeds as follows. Images captured to the computer 38 from the commercial ultrasound linear array scanner are used to form a volume image. The volume image is represented in computer software as a three-dimensional array of volume sample values, while two-dimensional images are represented by two-dimensional arrays of image values. In order to form a volume image from the captured images, one must perform interpolation from where the image samples fall in space to where one wants to locate the regular array of volume image values. This is the well-known mathematical problem of interpolation. In general, as is illustrated in FIG. 9, a volume value is calculated as the weighted sum of neighboring image values. The weights are chosen such that if the volume sample point falls exactly on one of the image points, the volume value is set equal to the value of the corresponding image value. Otherwise, the volume value will be computed to depend upon the contributing image values in inverse proportion to the distances of the particular image samples from the volume sample, or some other function of the distance.

Interpolation in three dimensions is a direct and well-known extension of methods designed for two dimensions in image processing as described for example in: Udupa, J. K., et al., 3D IMAGING IN MEDICINE, CRC Press, 1991; Foley, J. D., et al., COMPUTER GRAPHICS: PRINCIPLES AND PRACTICE, Second ed., Addison-Wesley, 1990; Foley, J. D., et al., FUNDAMENTALS OF INTERACTIVE COMPUTER GRAPHICS, Addison-Wesley, 1982; and, Gonzalez, R. C., et al., DIGITAL IMAGE PROCESSING, Addison-Wesley, 1992. It should be recalled that the scanner of the present invention acquires images in multiple sweeps across the paddle to cover the region of interest. The location of each image plane is known from the motion controller and the encoded Z axis position. Therefore, the spatial information is known for all planes for use in formulas to form a volume image. The volume image itself can be set to encompass all planes, or a subregion for a zoomed-in view.

Figure 10A:
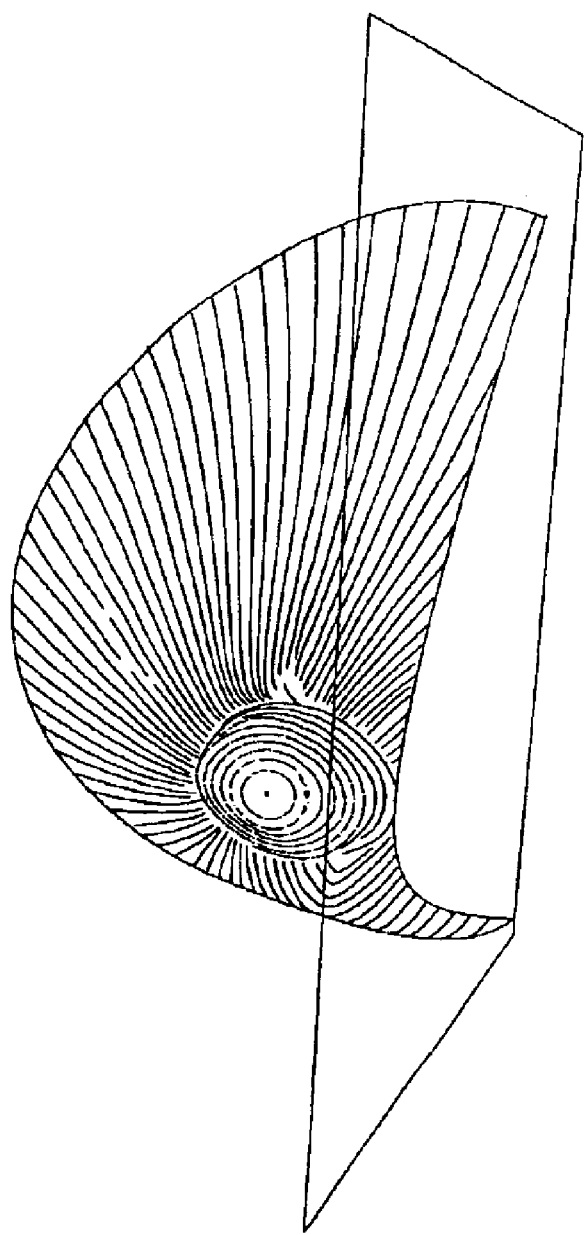
FIG. 10A, FIG. 10B, and FIG. 10C illustrate perpendicular plane views of a breast.
Figure 10B:
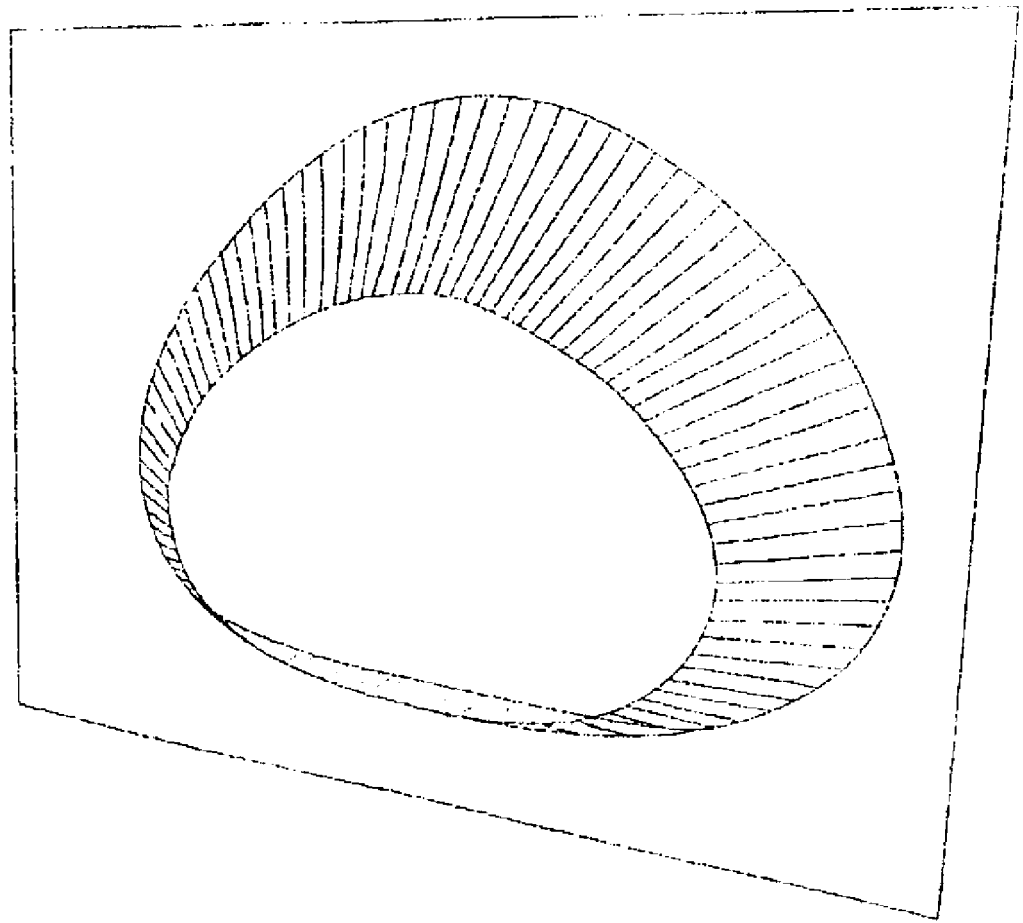
Figure 10C:
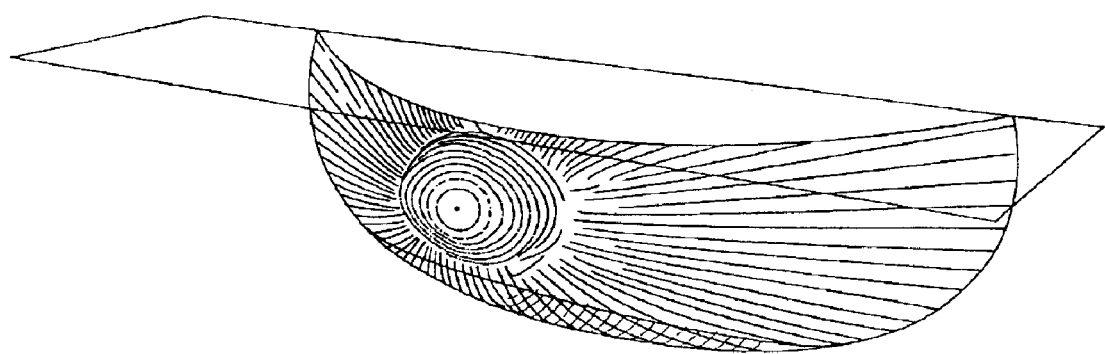
Figure 10D:
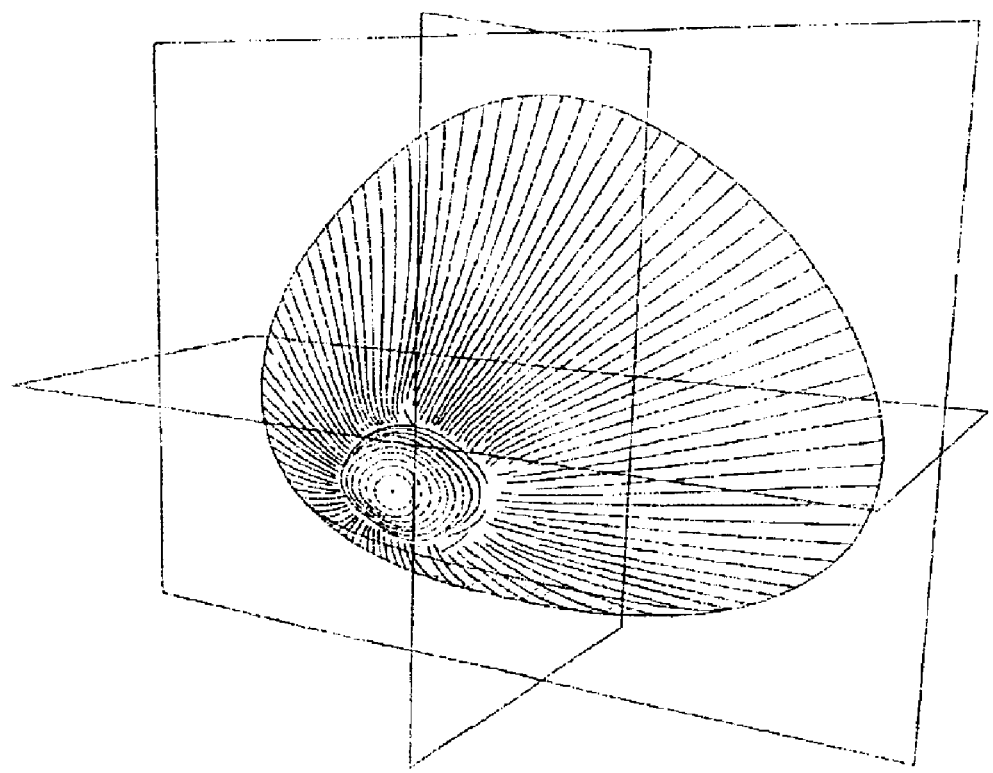
FIG. 10D illustrates a view of the intersection of perpendicular views of a breast.
Figure 11:
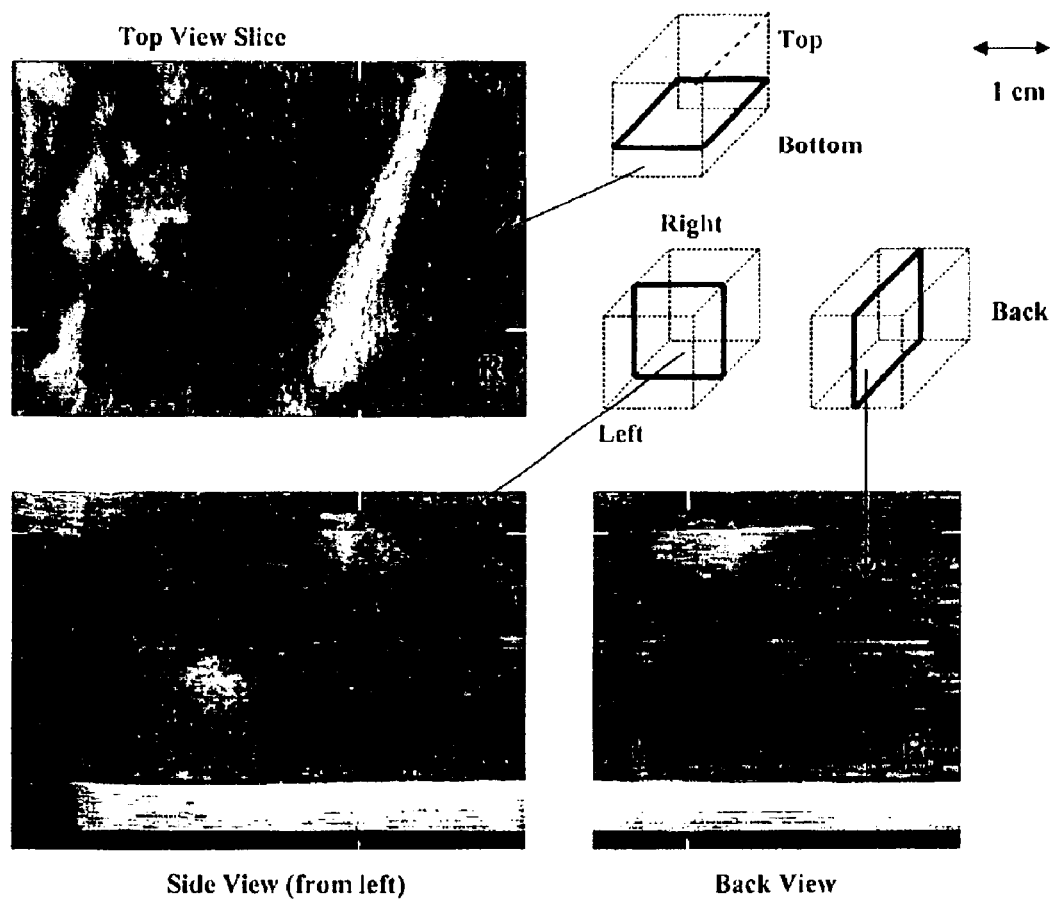
FIG. 11 illustrates a computer display of orthogonal plane views.
Figure 12:
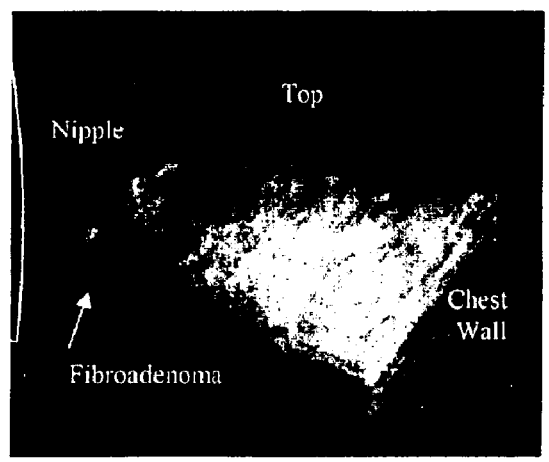
FIG. 12 illustrates a volume-rendering view.

The volumetric image is displayed in several formats on computer display 42 for comparison to the spatially-registered x-ray image. These include, but are not limited to, intersecting perpendicular or orthogonal planes of the breast (See FIG. 1A, FIG. 10B, FIG. 10C, FIG. 10D, and FIG. 11), and translucent volume-rendered views (See FIG. 12). Once a volume image is obtained, it can be displayed in a variety of formats on the computer display 42. One format which applicants' research has shown to be an effective approach is to show the intersection of the three individual perpendicular planes of a breast as illustrated in FIG. 10A, FIG. 10B, and FIG. 10C, and/or the intersection of the individual perpendicular planes as illustrated in FIG. 11D. A user interface implemented in computer software can employ a mouse to interactively select particular planes and to play them back in a movie loop which pages through slices in one particular direction. Many other formats can be used, as is well known in the three dimensional visualization art. Computer constructed intersecting perpendicular, or orthogonal plane views are illustrated in FIG. 11. Volume-rendered views, as illustrated in FIG. 12, are also generated with the aid of the computer 38.

Operation of systems constructed according to the present invention results in x-ray and ultrasound images that are in spatial registration. The medical practitioner can view the x-ray along with top-view planes or projected views of the volumetric ultrasound. Visually and mentally, the practitioner can then fuse, merge, or visualize the imaging modalities as qualitatively registered, and compare the same abnormality appearing in both. However, additional reference information is required for the computer 38 to quantitatively register image points, that is, for the operator to know that a point (X1, Y1) in an x-ray image is in the same spatial location in world coordinates as the projected or sliced ultrasound view at (X2, Y2), where (X1, Y1) and (X2, Y2) are relative to a reference coordinate frame. Software in a system constructed according to the present invention is designed to permit easy integration of this information, and to permit display of registered x-ray and ultrasound images side-by-side on the computer 38 monitor. It should thus be understood that the present invention can accept and be enhanced to perform quantitative registration given a particular physical registration target arrangement. In other words, specific registration approaches can be incorporated into the present invention. Prior art systems of the types illustrated and described in U.S. Pat. Nos. 5,474,072; 5,479,927; 5,640,956; 5,664,573; 5,938,613; 5,603,326; 5,776,062; and, 5,840,022 are described as producing registered images. However, the prior art does not develop specific computable referencing methods to support the claim that quantitative registration can be practically performed in multi-modal breast imaging by the prior art systems.

In another embodiment, the three-dimensional scanner is mounted to an independent support device, post, or articulated arm so that it can operate either in conjunction with x-ray mammography, other imaging systems, or independently, for three-dimensional ultrasound-only imaging. Many variations of supports, such as, for example, commercially available C-arms designed for medical imaging, can be employed to support the mechanical scanner 20. Any support which can position the scan assembly in the desired orientations can be used.

The stand-alone version can be used, for example, with an x-ray machine, or alone as an ultrasound-only imaging device, or with other suitable medical imaging modalities where a system constructed according to the present invention can be mounted to, or situated to interact with such imaging modality. The compression paddle 100 can be replaced by a flexible paddle or a flexible membrane of, for example, a rubber-like or elastomeric material. Because the Z position of the scanning probe 32 is encoded, the flexure of the paddle or membrane is sensed by the computer 38 and used to form accurate volumetric constructions. The apparatus and method of scanning illustrated and described herein can significantly decrease patient time and permit relatively precise correlation between x-ray mammograms and whole breast ultrasound examination. The evaluation of the entire scanning volume of a mass can significantly improve accuracy in diagnosis. It is believed that the close correlation of digital x-ray mammographic images with whole breast ultrasound made possible by the method and apparatus illustrated and described herein will lead to improved accuracy in detecting malignant breast masses.

Another technique for examination of the young breast was to replace the compression paddle and film holder of a standard x-ray mammography machine with ultrasound transparent paddles of the general types and configurations described above. The presence of two opposing ultrasound transparent paddles provided a number of advantages. For example, when imaging the breast in the craniocaudal position, it is also possible to ultrasonically scan the breast in the caudocranial position without making any changes to the C-arm positions. All that is necessary is to run the linear array transducer along the surface of the inferior paddle. Caudocranial scanning is of particular advantage for the large breasted patient with a mass that is located deep behind the anterior wall of the breast held in the craniocaudal position. In this situation, that mass is located close to the inferior aspect of the breast surface and can thus be readily visualized by a transducer scanning over the surface of the inferior paddle. An additional advantage of the caudocranial position is that the inferior aspect of the breast in this position is extremely flat. This permits direct, that is, perpendicular, entrance of the ultrasound beam. This normal angle of incidence has an advantage in terms of non-divergence of the beam on entry. An additional advantage is that the ultrasound beam entering via the flat inferior breast surface can image all of the tissues in its path including the nipple-areola region. This is one solution to the problem of difficulties encountered when scanning across the anteriorly located compression paddle in the craniocaudal position, namely, the failure to image the nipple-areola because of lack of contact between the nipple-areola and the compression paddle.

In the oblique positions or any of the lateral positions, the double ultrasound transmitting paddle permits imaging from whichever orientation is most advantageous. For example, in the lateral position the ultrasound beam may enter the breast form either the medial or lateral side. This ability to ultrasonically image the breast in various orientations improves correlation between ultrasound and x-ray mammography images. Again, this approach can be implemented in either 2D or 3D imaging.

We claim:

1. A method for examining a breast of a subject, the method comprising the steps of:
   providing an apparatus including
      a compression paddle constructed from a plastic material, the paddle comprising a first surface against which the breast is compressed and a second surface opposite the first surface,
      an ultrasound probe for generating ultrasound image data of the breast through the material of the compression paddle and in spatial registration with the compression paddle,
      a motion control system for movement of the probe in relation to the compression paddle and for sensing the probe's position, the motion control system comprising a Z-axis positioner for movement of the probe in a dimension perpendicular to the compression paddle, and
      a computer for generating an ultrasound image from the ultrasound image data and from information regarding the spatial registration;
   compressing the breast with the paddle causing the breast to be in contact with the first surface of the paddle; and
   generating ultrasound image data of the compressed breast through the plastic material of the compression paddle utilizing the motion control system for movement of the probe in relation to the compression paddle, wherein the Z-axis positioner is utilized for maintaining contact of the probe with the second surface of the paddle.

2. The method of claim 1, further comprising the steps of:
   providing an x-ray tube for generating x-ray data; and
   generating x-ray data of the compressed breast.

3. The method of claim 2, further comprising the steps of:
   providing a computer operably connected to the ultrasound probe and to the x-ray tube; and
   receiving the ultrasound image data and the x-ray data with the computer.

4. The method of claim 1, wherein the step of generating the ultrasound image data further requires engagement of the X-axis actuator and Y-axis actuator to generate ultrasound image data comprising two dimensions.

5. The method of claim 1, wherein the step of generating the ultrasound image data further requires engagement of the X-axis actuator and Y-axis actuator to generate ultrasound image data comprising three dimensions.

6. The method of claim 1, wherein the step of utilizing the motion control system further requires that the motion control system utilize the Z-axis positioner for maintaining contact of the probe with the second surface of the paddle by movement in a direct perpendicular to the X-axis and Y-axis actuators.

7. The method of claim 6, wherein the step of generating the ultrasound image data further requires engagement of the first and second axis control to generate ultrasound image data comprising two dimensions.

8. The method of claim 7, further comprising the steps of:
   adjusting the third axis control; and
   repeating the step of generating the ultrasound image data to generate ultrasound image data comprising three dimensions.

9. The method of claim 8, further comprising the steps of:
repeating the steps of adjusting the third axis control; and
generating the ultrasound image data to generate ultrasound image data comprising three dimensions until substantially all of the breast is represented by such ultrasound image data.

10. The method of claim 6, wherein the step of providing a motion control system further requires that the first, second, and third axis controls be automatically actuated.

11. The method of claim 1, wherein the step of providing a motion control system further requires that at least one of the first axis control or third axis control is manually actuated.

12. The method of claim 1, wherein the step of providing a motion control system further requires that at least one of the X-axis actuator, Y-axis actuator, or Z-axis positioner is automatically actuated.

13. The method of claim 1, wherein the paddle has a thickness between about 0.02 inch (about 0.5 mm) to about 0.12 inch (about 3 mm), the method further comprising the step of:
providing a transducer operably connected to the probe for generating an ultrasound beam from which the ultrasound image data is generated, the ultrasound beam having a frequency greater than about 5 MHz.

14. A method for generating an ultrasound image of a compressed breast of a subject, the method comprising the steps of:
providing an apparatus including
a compression paddle constructed from a plastic material, the paddle comprising a first surface against which the breast is compressed and a second surface opposite the first surface,
an ultrasound probe for generating ultrasound image data of the breast through the material of the compression paddle and in spatial registration with the compression paddle,
a motion control system for movement of the probe in relation to the compression paddle and for sensing the probe's position, the motion control system including a Y-axis actuator, an X-axis actuator, and a Z-axis positioner for movement of the probe in three dimensions;
compressing the breast with the paddle causing the breast to be in contact with the first surface of the paddle; and
scanning the breast with the ultrasound probe through the material of the compression paddle utilizing the motion control system for movement of the probe in relation to the compression paddle, wherein the Z-axis positioner is utilized for maintaining contact of the probe with the second surface of the paddle.

15. The method of claim 14, further comprising the step of:
adjusting one of the first-axis control or the second-axis control.

16. The method of claim 15, further comprising the step of:
repeating the step of scanning the breast.

17. A method for generating an ultrasound image and an x-ray image of a compressed breast of a subject, the method comprising the steps of:
providing an apparatus comprising
an x-ray mammography unit for generating the x-ray image, the x-ray mammography unit including a compression paddle,
a vertical x-ray support column having a movable arm supporting an x-ray tube,
a compression paddle mount block movable along the vertical x-ray support column, the compression paddle connected to the compression paddle mount block and being both radiolucent and sonolucent, and the paddle comprising a first surface against which the breast is compressed and a second surface opposite the first surface,
an ultrasound scanner connected to the compression paddle mount block, the scanner comprising an ultrasound probe for generating ultrasound image data in spatial registration with the compression paddle, a motion control system for movement of the probe in spatial relation to the compression paddle and for sensing the probe's position, the motion control system including a Z-axis-controller for controlling the movement of the probe toward contact with the compression paddle, and
an x-ray detector assembly including an x-ray image detector and a lower support surface for supporting a compressed breast;
compressing the breast with the paddle causing the breast to be in contact with the first surface of the paddle;
scanning the compressed breast with the ultrasound scanner utilizing the motion control system for movement of the probe in relation to the compression paddle, wherein the Z-axis controller is utilized for maintaining contact of the probe with the second surface of the paddle; and
scanning the compressed breast with the x-ray tube.

18. The method of claim 17, further comprising the step of:
adjusting the motion control system.

19. The method of claim 18, further comprising the step of:
repeating the step of scanning the compressed breast with the ultrasound scanner.

20. The method of claim 17, wherein the step of providing an apparatus further requires that the apparatus include a computer operably connected to the scanner and the x-ray mammography unit for receipt of the ultrasound image data and the x-ray image.

21. A method for examining a breast of a subject, the method comprising the steps of:
providing an apparatus including
a compression paddle suitable for contacting a surface of the breast, the compression paddle being both radiolucent and sonolucent, and of a thickness between about 0.02 inch (about 0.5 mm) to about 0.12 inch (about 3 mm), and constructed of polycarbonate plastic,
a device for applying pressure to the surface of the breast with the compression paddle to compress the breast to reduce the thickness of the breast tissue,
a transducer for generating an ultrasound beam having a frequency greater than about 5 MHz for transmission through the compression paddle and the compressed breast tissue and for receiving echoes from the compressed breast tissue through the compression paddle, and
a device for converting the received echoes into breast imaging data;
compressing the breast; and
scanning the breast with the transducer.

* * * * *